US007030051B2

(12) United States Patent
Davies

(10) Patent No.: US 7,030,051 B2
(45) Date of Patent: Apr. 18, 2006

(54) DIRHODIUM CATALYST COMPOSITIONS AND METHODS FOR USING SAME

(75) Inventor: Huw M. L. Davies, Clarence Center, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 134 days.

(21) Appl. No.: 10/229,378

(22) Filed: Aug. 27, 2002

(65) Prior Publication Data

US 2003/0130536 A1 Jul. 10, 2003

Related U.S. Application Data

(60) Provisional application No. 60/315,150, filed on Aug. 27, 2001.

(51) Int. Cl.
*B01J 31/00* (2006.01)
(52) U.S. Cl. .................. 502/150; 518/701; 423/22; 252/182.33; 502/127; 502/166
(58) Field of Classification Search ................ 502/150, 502/127, 166; 518/701; 423/22; 252/182.33
See application file for complete search history.

(56) References Cited

U.S. PATENT DOCUMENTS

| 2,507,631 | A | | 5/1950 | Hartmann et al. |
| 2,957,880 | A | | 10/1960 | Rometsch et al. |
| 4,133,881 | A | | 1/1979 | Cale, Jr. et al. |
| 4,238,488 | A | | 12/1980 | Howe et al. |
| 4,866,048 | A | | 9/1989 | Calverley et al. |
| 5,036,053 | A | | 7/1991 | Himmelsbach et al. |
| 5,175,311 | A | | 12/1992 | Doyle |
| 5,296,595 | A | | 3/1994 | Doyle |
| 5,302,737 | A | * | 4/1994 | Doyle et al. ................. 556/436 |
| 5,401,732 | A | | 3/1995 | Calverley et al. |
| 5,591,854 | A | * | 1/1997 | Davies ......................... 546/14 |
| 5,665,890 | A | | 9/1997 | Jacobsen et al. |
| 5,760,055 | A | | 6/1998 | Davies |
| 5,789,333 | A | | 8/1998 | Angelici et al. |
| 6,025,502 | A | * | 2/2000 | Winklter et al. ............... 549/21 |
| 6,410,746 | B1 | * | 6/2002 | Davies ........................ 548/403 |
| 6,420,304 | B1 | * | 7/2002 | Tsai et al. .................... 502/207 |

FOREIGN PATENT DOCUMENTS

GB       2 260 903 A     5/1993
WO       WO 00/64583    11/2000

OTHER PUBLICATIONS

Doyle, et al. "Dirhodium (II) Tetrakis[methyl 2-oxaazetidine-4-carboxylate]: A Chiral Dirhodium (II) Carboxamidate of Exception Reactivity and Selectivity", Organic Letters 2(8), 1145-1147.*

Bertilsson et al. "A Rigid Dirhodium (II) Carboxylate as an Efficient Catalyst for the Asymmetric Cyclopropanation of Olefins", J. Organometallic Chemistry 603 (2000), 13-17.*
Davies et al. "Kinetic Resolution and Double Stereodifferentiation in Catalytic Asymmetric C-H Activation of 2-Substituted Pyrrolidines", Organic Letters 3(11), 1773-1775.*
Doyle et al. "Cyclopropanation versus carbon-hydrogen insertion. The influences of substrate and catalyst on selectivity", Tetrahedron Letters 42 (2001), 3155-3158.*
Davies, et al. "Conformational analysis and stereochemical assignments of products from C-H activation at secondary sites", Tetrahedron Letters 42 (2001), 3149-3151.*
Bulugahapitiya, et al. "A Stereospecific Access to Alylic Systems Using Rhodium (II)-Vinyl Carbenoid Insertion into Si-H, O-H, and N-H Bonds", J. Org. Chem. 62 (1997), 1630-1641.*
Aggarwal, et al. "Catalytic Cyclopropanation of Alkenes Using Diazo Compounds Generated in Situ. A Novel Route to 2-Acrylcyclopropylamines", Organic Letters 3(17) 2785-2788.*
Davies et al., "Asymmetric Cyclopropanations by Rhodium (II) N-(Arylsulfonyl)prolinate Catalyzed Decomposition of Vinyldiazomethanes in the Presence of Alkenes. Practical Enantioselective Synthesis of the Four Isomers of 2-Phenylcyclopropan-1-amino Acid," *J. Am. Chem. Soc.*, 118 (29):6897-6907 (1996).
Davies et al., "Effect of Diazoalkane Structure on the Stereoselectivity of Rhodium (II) (S)-N-(Arylsulfonyl) prolinate Catalyzed Cyclopropanations," *Tetrahedron Letters*, 37(24):4133-4136 (1996).
Deutsch, et al., "Synthesis and Pharmacology of Potential Cocaine Antagonists. 2. Structure—Activity Relationship Studies of Aromatic Ring-Substituted Methylphenidate Analogs," *J. Med. Chem.*, 39:1201-1209 (1996).

(Continued)

*Primary Examiner*—J. A. Lorengo
*Assistant Examiner*—Jennine Brown
(74) *Attorney, Agent, or Firm*—Rogalskyj & Weyand, LLP

(57) ABSTRACT

Disclosed is method for increasing the efficiency of a dirhodium catalyst. The method includes providing a dirhodium catalyst, providing an organic ester, and contacting the dirhodium catalyst and the organic ester under conditions effective to increase the efficiency of the dirhodium catalyst. The organic ester is selected such that it is not a substrate for catalysis by the dirhodium catalyst. Dirhodium catalyst compositions which include a dirhodium catalyst and an organic ester are also disclosed. In these compositions, the organic ester is not a substrate for catalysis by the dirhodium catalyst. The method and compositions can be used in a number of reactions, including insertion reactions (e.g., C—H insertions, Si—H insertions, O—H insertions, and N—H insertions) cyclopropanation reactions, annulations (e.g., [3+2] annulations and [3+4] annulations), and ω,ω-diarylalkanoate syntheses.

27 Claims, No Drawings

OTHER PUBLICATIONS

Doyle et al., "Chiral Catalysts for Enantioselective Intermolecular Cyclopropanation Reactions With Methyl Phenyldiazoacetate. Origin of the Solvent Effect in Reations Catalyzed by Homochiral Dirhodium(II) Prolinates," *Tetrahedron Letters*, 37(24):4129-4132 (1996).

Davies et al., "Asymmetric Intermolecular Carbenoid C-H Insertions Catalyzed by Rhodium(II) (S)-N-(p-Dodecylphenyl)sulfonylprolinate," *J. Am. Chem. Soc.*, 119: 9075-9076 (1997).

Davis, "Asymmetric Synthesis Using Rhodium-Stabilized Vinylcarbenoid Intermediates," *Aldrichimica Acta*, 30 (4): 107-114 (1997).

Davies et al., "Enantioselective Synthesis of Functionalized Tropanes by Rhodium(II) Carboxylate-Catalyzed Decomposition of Vinyldiazomethanes in the Presence of Pyrroles," *Journal of Organic Chemistry*, 62(4):1095-1105 (1997).

Davies et al., "Synthesis and Evaluation of a Novel Dirhodium Tetraprolinate Catalyst Containing Bridging Prolinate," *Tetrahedron Letters*, 38(24):4203-4206 (1997).

Axten, et al., "A Stereoselective Synthesis of dl-threo-Methylphenidate: Preparation and Biological Evaluation of Novel Analogues," *J. Org. Chem.*, 63:9628-9629 (1998).

Davies et al., "Effect of Carbenoid Structure on the Reactivity of Rhodium Stabilized Carbenoids," *Tetrahedron Letters*, 39:4417-4420 (1998).

Davies et al., "Effect of Catalyst on the Diastereoselectivity of Metal Phenyldiazoacetate Cyclopropanations," *Tetrahedron Letters*, 39:8811-8812 (1998).

Davies, "Rhodium-Stabilized Vinylcarbenoid Intermediates in Organic Synthesis," *Current Organic Chemistry*, 2:463-488 (1998).

Davies et al., "Tandem Asymemtric Cyclopropanation/Cope Rearrangement. A Highly Diastereoselective and Enantioselective Method for the Construction of 1,4-Cycloheptadienes," *J. Am. Chem. Soc.*, 120(14):3326-3331 (1998).

Stinson, "Counting on Chiral Drugs," *Chemical & Engineering News*, pp. 83ff (Sep. 21, 1998).

Thai et al., "Asymmetric Synthesis and Pharmacology of Methylphenidate and Its Para-Substituted Derivatives," *J. Med. Chem.*, 41:591-601 (1998).

Axten, et al., "Enantlioselective Synthesis of D-threo-Methylphenidate," *J. Am. Chem. Soc.*, 121(27):6511-6512 (1999).

Davies, "[3+4] Annulations Between Rhodium-stabilized Vinylcarbenoids and Dienes," *Advances in Cycloaddition*, 5:119-164 (1999).

Davies, et al. "Catalytic Asymmetric Synthesis of Diarylacetates and 4,4-Diarylbutanoates. A Formal Asymmetric Synthesis of (+)- Sertraline," *Organic Letters*, 1(2): 233-236 (1999).

Davies, et al., "Catalytic Asymmetric Synthesis of Syn-Aldol Products from Intermolecular C-H Insertions Between Allyl Silyt Ethers and Methyl Aryldiazoacetates," *Organic Letters*, 1(3):383-385 (1999).

Davies, "Dirhodium Tetra(N-arylsulfonylprolinates) as Chiral Catalysts For Asymmetric Transformations of Vinyl- and Aryldiazoacetates," *Eur. J. Org. Chem.*, 2459-2469 (1999).

Davies et al., "Enantioselective Synthesis of Fused Cycloheptadienes by a Tandem Intramolecular Cyclopropanation/Cope Rearrangement Sequence," *J. Org. Chem.*, 64(23):8501-8508 (1999).

Davies et al., "Highly Regio-, Diastereo-, and Enantioselective C-H Insertions of Methyl Aryldiazoacetates into Cyclic N-Boc-Protected Amines. Asymmetric Synthesis of Novel C2-Symmetric Amines and threo-Methylphenidate," *J. Am. Chem Soc.*, 121(27):6509-6510 (1999).

Davies, et al., "Novel Dirhodium Tetraprolinate Catalysts Containing Bridging Prolinate Ligands for Asymmetric Carbenoid Reactions," *Tetrahedron Letters*, 40:5287-5290 (1999).

Deutsch, et al., "Synthesis and Pharmacology of Site-Specific Cocaine Abuse Treatment Agents: 2-(Aminomethyl)-3-phenylbicyclo[2.2.2]-and -[2.2.1]alkane Dopamine Uptake Inhibitors,"*J. Med. Chem.*, 42:882-895 (1999).

Deutsch et al., "Synthesis and Pharmacology of Site-Specific Cocaine Abuse Treatment Agents: The Role of the Phenyl Group to Highly Modified Methylphenidate Analogs As Dopamine Uptake Inhibitors," *Medicinal Chemistry Research*, 9(4):213-222 (1999).

Matsumura, et al., "A Convenient Method for Synthesis of Enantiomerically Enriched Methylphenidate from N-Methoxycarbonylpiperidine," *Organic Letters*, 1(2):175-178 (1999).

Prashad, et al., "Enantioselective Synthesis of (2S,2'R)-erythro-methylphenidate," *Tetrahedron: Asymmetry*, 10: 3479-3482 (1999).

Prashad, et al., "The First Enantlioselective Synthesis of (2R,2'R)-threo-(+)-Methylphenidate Hydrochloride," *J. Org. Chem.*, 64:1750-1753 (1999).

Davies, et al., "Catalytic Asymmetric C-H Activation of Alkanes and Tetrahydrofuran," *J. Am. Chem. Soc.*, 122(13): 3063-3070 (2000).

Davies et al., "Catalytic Asymmetric Synthesis of Diarylacetates and 4,4-Diarylbutanoates. A Formal Asymmetric Synthesis of (+)-Sertraline," *Organic Letters*, 2(3): 417-417 (2000).

Davies et al., "Effect of Rhodium Carbenoid Structure on Cyclopropanation Chemoselectivity," Tetrahedron, 56: 4871-4880 (2000).

Davies, et al., "Effect of Carbenoid Structure on the Reactions of Rhodium-Stabilized Carbenoids with Cycloheptatriene," *Tetrahedron Letters*, 41:2035-2038 (2000).

Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters*, 2(6):823-826 (2000).

Dias et al., "Short Synthesis of Methylphenidate and Its p-Methoxy Derivative," *Synthetic Communications*, 30(7): 1311-1318 (2000).

Müller et al., "Intermolecular Cyclopropanation Versus CH Insertion in RhiI-Catalyzed Carbenoid Reactions," *Tetrahedron*, 56:1725-1731 (2000).

Davies et al., "Asymmetric Intramolecular C-H Insertions of Aryldiazoacetates," *Organic Letters*, 3(10):1475-1477 (2001).

Davies et al., "Catalytic Asymmetric C-H Activation of Silyl Enol Ethers as an Equlvalent of Asymmetric Michael Reaction," *J. Am. Chem. Soc.*, 123(9):2070-2071 (2001).

Davies et al., "Catalytic Asymmetric Synthesis of Highly Functionalized Cyclopentenes by a [3+2] Cycloaddition," *J. Am. Chem. Soc.*, 123(30):7461-7462 (2001).

Davies et al., "Improved Dirhodium Tetraprolinate Catalysts for Asymmetric Reactions of Diazocarbonyl Compounds," abstract No. 249 in *Abstracts of the 222nd ACS National Meeting, Chicago, Illinois, Aug. 26-30, 2001*, American Chemical Society, Division of Organic Chemistry (2001).

Davies et al., "Kinetic Resolution and Double Stereodifferentiation in Catalytic Asymmetric C-H Activation of 2-Substituted Pyrrolidines," *Organic Letters*, 3(11):1773-1775 (2001).

Davies et al., "Recent Progress in Asymmetric Intermolecular C-H Activation by Rhodium Carbenoid Intermediates," *J. Organometallic Chem.*, 617-618:47-55 (2001).

Colacot, "An Overview on the Applications of 'Doyle Catalysts' in Asymmetric Cyclopropanation, Cyclopropenation and C-H Insertion Reactions," *Proc. Indian Acad. Sci. (Chem. Sci.)*, 112(3):197-207 (2000).

Doyle et al., "A New Approach to Macrocyclization Via Alkene Formation in Catalytic Diazo Decomposition. Synthesis of Patulolides A and B," *Organic Letters*, 2(12): 1777-1779 (2000).

Doyle et al., "Dirhodium(II) Tetrakis[methyl 2-oxaazetidine-4-carboxylate]: A Chiral Dirhodium(II) Carboxamidate of Exceptional Reactivity and Selectivity," *Organic Letters*, 2(8):1145-1147 (2000).

Doyle et al., "Enantiocontrolled Macrocycle Formation by Catalytic Intramolecular Cyclopropanation," *J.Am. Chem. Soc.*, 122:5718-5728 (2000).

Doyle et al., "Selectivity in Reactions of Allyl Diazoacetates as a Function of Catalyst and Ring Size From -Lactones to Macrocyclic Lactones," *J. Org. Chem.*, 65:8839-8847 (2000).

Doyle et al., "A New Class of Chiral Lewis Acid Catalysts for Highly Enantioselective Hetero-Diels-Alder Reactions: Exceptionally High Turnover Numbers from Dirhodium(II) Carboxamidates," *J. Am. Chem. Soc.*, 123:5366-5367 (2001).

Doyle et al., "Epoxides and Aziridines From Diazoacetates Via Ylide Intermediates," *Organic Letters*, 3(6):933-935 (2001).

\* cited by examiner

DIRHODIUM CATALYST COMPOSITIONS AND METHODS FOR USING SAME

This application claims the benefit of U.S. Provisional Patent Application Ser. No. 60/315,150, filed Aug. 27, 2001, which is hereby incorporated by reference.

The present invention was made with the support of the National Science Foundation, Contract No. CHE 0092490, and the National Institutes of Health, Contract No. CA85641 and Contract No. GM57425. The Federal Government may have certain rights in this invention.

FIELD OF THE INVENTION

The present invention relates, generally, to metal catalyst compositions and to methods for using such compositions and, more particularly, to dirhodium catalyst compositions and to methods for using such compositions.

BACKGROUND OF THE INVENTION

Dihodium catalysts have been employed as catalysts in a variety of chemical reactions. One of the major drawbacks of using dirhodium catalysts is the expense of rhodium metal. Typically, to overcome the costs associated with catalysts containing expensive metals, two approaches can be used: (i) increasing the efficiency (e.g., turnover number and/or turnover rate) of the catalyst and/or (ii) recovering the spent catalyst from the reaction mixture so that the expensive metal can be separated and recycled. Neither approach has had much success with chiral dirhodium catalysts.

The present invention is directed to methods for increasing the efficiency of dirhodium catalysts and to methods and compositions that are useful in carrying out dirhodium-catalyzed reactions.

SUMMARY OF THE INVENTION

The present invention relates to a method for increasing the efficiency of a dirhodium catalyst. The method includes providing a dirhodium catalyst, providing an organic ester, and contacting the dirhodium catalyst and the organic ester under conditions effective to increase the efficiency of the dirhodium catalyst. The organic ester is selected such that it is not a substrate for catalysis by the dirhodium catalyst.

The present invention also relates to a dirhodium catalyst composition which includes a dirhodium catalyst and an organic ester, and the organic ester is not a substrate for catalysis by the dirhodium catalyst.

DETAILED DESCRIPTION OF THE INVENTION

The present invention relates to a method for increasing the efficiency of a dirhodium catalyst. The method includes providing a dirhodium catalyst, providing an organic ester, and contacting the dirhodium catalyst and the organic ester under conditions effective to increase the efficiency of the dirhodium catalyst. The organic ester is selected such that it is not a substrate for catalysis by the dirhodium catalyst.

As used herein, a catalyst's "efficiency" is meant to be viewed as being increased if the catalyst's turnover number is increased, if the catalyst's turnover rate is increased, or both. As used herein, for a given set of reaction conditions, a catalyst's "turnover number" is the number of moles of product formed per gram-atom of rhodium present in the reaction, and a catalyst's "turnover rate" is the number of moles of product produced per unit time. Although it is generally desirable to employ reaction conditions which maximize a catalyst's turnover number and/or turnover rate, any degree of increase in a catalyst's turnover number and/or turnover rate is beneficial, especially in view of the high cost of rhodium. Accordingly, as used herein, "increase" and "increasing" are meant to include any measurable increase in the dirhodium catalyst's efficiency (e.g., any measurable increase in turnover number and/or turnover rate), such as, for example, an increase of greater than about 0.5%, an increase of greater than about 1%, an increase of greater than about 5%, an increase of greater than about 10%, an increase of greater than about 50%, an increase of greater than about 100%, an increase of greater than about 1000%, an increase of greater than about 9000%, and/or an increase of greater than about 100000% in turnover number and/or turnover rate.

As used herein, organic ester is meant to include esters of carboxylic acids, such as esters of an aryl acid (e.g., esters of a benzoic acid (which is meant to include unsubstituted as well as substituted benzoic acid) or of a naphthoic acid (which is meant to include unsubstituted as well as substituted naphthoic acids)). The aromatic portion of the aryl ester can be substituted with, for example, halogen, an alkyl group, an aromatic group, and other substituents which do not appreciably interact with the reactants being employed and which do not adversely effect the dirhodium catalyst. Furthermore, the organic ester is selected such that it is not a substrate for catalysis by the dirhodium catalyst. As used herein, an organic ester is to be deemed "not a substrate for catalysis by the dirhodium catalyst" if and only if it is not a reactant in a reaction catalyzed by the dirhodium catalyst. Illustratively, the organic ester can be a C1–C12 alkyl (e.g., a methyl, an ethyl, a 2-chloroethyl, an n-propyl, an i-propyl, an n-butyl, an i-butyl, a t-butyl, a cyclohexyl, a 2-phenylethyl, a benzyl, etc.) ester of a benzoic acid. Organic esters having the formula $C_6H_5COOW$ where W is a C1–C12 alkyl group are illustrative, as are organic esters having the formula $C_6H_5COOW$ and where W is a C1–C4 alkyl group, such as a methyl group. "Organic ester", as used herein, is also meant to include combinations of such esters, as well as organic esters other than particular organic esters, such as organic esters other than C1–C4 acetates and/or other than ethyl acetate. "Organic ester" is also meant to include those organic esters which contain no transition metal; those organic esters which contain no metal (transition or otherwise); those organic esters which contain no elements other than C, H, N, O, S, Se, F, Cl, Br, and I; as well as those organic esters which contain no elements other than C, H, and O.

As used herein, "alkyl" is meant to include linear alkyls, branched alkyls, and cycloalkyls, each of which can be substituted or unsubstituted. "Alkyl" is also meant to include lower linear alkyls (e.g., C1–C6 linear alkyls), such as methyl, ethyl, n-propyl, n-butyl, n-pentyl, and n-hexyl; lower branched alkyls (e.g., C3–C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3–C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl".

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings and furanyl rings. The aromatic rings can be optionally substituted. "Aryl" is also meant to include aromatic rings to which are fused one or more other aryl rings or non-aryl rings. For example, naphthyl groups, indole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" refers to a homocyclic or heterocyclic ring which can be saturated or unsaturated. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

As used herein, "dirhodium catalyst" is meant to include any material which is or can be used as a catalyst which contains two rhodium atoms and/or ions that are bonded with one another. The nature of the bond is not limitative: it can be covalent, ionic, van der Walls, pi-pi, sigma-pi, etc., or combinations of these. Of course, the dirhodium catalyst can include other atoms or ions or groups of atoms (e.g., ligands). "Dirhodium catalyst" is also meant to include dirhodium or dirhodium-containing compounds that are attached to surfaces, such as dirhodium complexes which contain one or more ligands that is or are bonded (directly or indirectly) to a surface. Illustratively, each rhodium in the dirhodium catalyst can have a formal charge of +2, and the charge on the overall complex can be neutral.

Examples of suitable dirhodium catalysts include catalysts having the formula $L_4Rh$—$RhL_4$ where each of the L's is the same or different and represents a coordinating atom from one or more ligands.

For example, the dirhodium catalyst can be a dirhodium tetracarboxylate catalyst (i.e., a catalyst having the formula $L_4Rh$—$RhL_4$ where each of the L's represents a carboxylate oxygen from one of four carboxylate groups.

Examples of dirhodium tetracarboxylate catalysts include dirhodium acetate dimer, dirhodium propionate dimer, dirhodium butyrate dimer, dirhodium pentanoate dimer, dirhodium hexanoate dimer, dirhodium heptanoate dimer, dirhodium octanoate dimer, fluorinated analogs thereof (e.g. dirhodium heptafluorobutyrate dimer), and combinations thereof.

Other illustrative examples of dirhodium tetracarboxylate catalysts include those having the formula ("Formula I"):

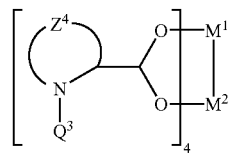

In Formula I, each of $M^1$ and $M^2$ is Rh. $Z^4$ represents the atoms necessary to complete a 3–12 membered heterocyclic ring, such as an alkylene moiety (e.g., a —$CH_2CH_2CH_2$— moiety). $Q^3$ is an electron withdrawing group, such as a group having the formulae —$C(O)R^9$, —$SO_2R^9$, or —$P(O)R^9R^{9'}$, where each of $R^9$ and $R^{9'}$ is independently selected from an alkyl group, an aryl group, and an alkoxy group.

As used herein, "electron withdrawing group" refers to those groups which are able to withdraw electron density from adjacent positions in a molecule, as determined, for example, by reference to the tables in the classical works which establish the classification of various substituents according to their electron withdrawing character. For example, reference may be made to the classification established by the Hammett scale, such as the one set forth in Gordon et al., *The Chemist's Companion*, New York: John Wiley & Sons, pp. 145–147 (1972) ("Gordon"), which is hereby incorporated by reference. Suitable electron-withdrawing groups include those having a para a value higher than or equal to about 0.2 or higher than or equal to about 0.3, with reference to the Hammett scale. Particular examples of electron withdrawing groups are moieties having the formulae —C(O)R, —$SO_2R$, and —P(O)RR', where R and R' are independently selected from an alkyl group, an aryl group, and an alkoxy group.

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—), eth-1,2-diyl (i.e., —CH$_2$CH$_2$—), prop-1,1-diyl (i.e., —CH(CH$_2$CH$_3$)—), prop-1,2-diyl (i.e.,—CH$_2$—CH(CH$_3$)—), prop-1,3-diyl (i.e., —CH$_2$CH$_2$CH$_2$—), prop-2,2-diyl (e.g. —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but- 2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group, such as moieties having the formula:

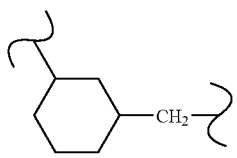

In Formula I and in all other formulae set forth in this document which contain one or more chiral centers and which do not specify the stereochemistry of a particular chiral center, such formulae are to be construed as encompassing all possible stereochemistries. Thus, for example, Formula I is meant to include (i) compounds in which the unspecified chiral center is entirely in the R configuration, (ii) compounds in which the unspecified chiral center is entirely in the S configuration, and (iii) racemic and other mixtures of (i) and (ii). Illustratively, dirhodium tetracarboxylate catalysts of Formula I are meant to include substantially chirally pure catalysts having one of the following formulae ("Formula II-A" and "Formula II-B", respectively):

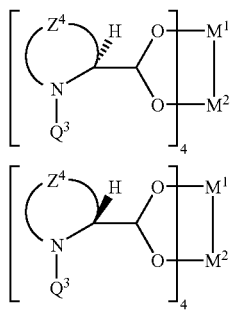

as well as dirhodium tetracarboxylate catalysts of Formula I having $D_2$ symmetry. Molecules having $D_2$ symmetry are molecules which have a vertical $C_2$ axis and a set of two $C_2$ axes perpendicular to the vertical $C_2$ axis. $D_2$ symmetry is further described in, for example, Cotton et al., *Advanced Inorganic Chemistry*, 4th ed., New York: John Wiley & Sons, pages 28–46 (1980), which is hereby incorporated by reference.

Specific examples of suitable catalysts having Formulae I and II include: $Rh_2(DOSP)_4$, $Rh_2(S\text{-}DOSP)_4$, and $Rh_2(R\text{-}DOSP)_4$, which are compounds having Formulae I, II-A, and II-B, respectively, in which each of $M^1$ and $M^2$ is Rh, $Z^4$ is a —CH$_2$CH$_2$CH$_2$— group, and $Q^3$ represents a 4-dodecylphenylsulfonyl moiety; and $Rh_2(TBSP)_4$, $Rh_2(S\text{-}TBSP)_4$, and $Rh_2(R\text{-}TBSP)_4$, which are compounds having Formulae I, II-A, and II-B, respectively, in which each of $M^1$ and $M^2$ is Rh, $Z^4$ is a —CH$_2$CH$_2$CH$_2$— group, and $Q^3$ represents a 4-t-butylphenylsulfonyl moiety. These and other illustrative compounds having Formulae I, II-A, and II-B are described in greater detail in Davies, "Rhodium-Stabilized Vinylcarbenoid Intermediates in Organic Synthesis," *Current Organic Chemistry*, 2:463–488 (1998), which is hereby incorporated by reference.

Other suitable dirhodium tetracarboxylate catalysts include those which contain two rhodium atoms or ions that are bonded to one another along an axis. This can be represented by the formula Rh—Rh, where the dash represents the bond and the bond axis. These catalysts also contain two carboxylate ligands. As used herein, "carboxylate ligands" means ligands which contain one or more carboxylate groups. As used herein, carboxylate groups mean groups having the formula:

which can be written with the following formula:

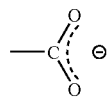

where the dashed line represents the delocalized electrons. Alternatively, the carboxylate group can be expressed without showing the delocalized electrons, as in the following formula:

Each of the two carboxylate ligands includes two carboxylate groups, and these two carboxylate groups are bonded to each other via a moiety having the formula ("Formula III"):

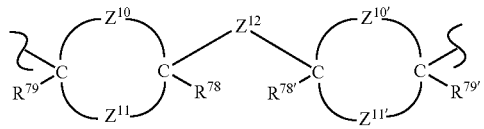

In Formula III, $Z^{10}$ and $Z^{11}$, together with the atoms to which they are bonded form a 3–12 membered ring, and $Z^{10'}$ and $Z^{11'}$, together with the atoms to which they are bonded form a 3–12 membered ring. $Z^{10}$ and $Z^{10'}$ can be the same, and each can contain a heteroatom, such as a nitrogen, oxygen, or sulfur. For example in one embodiment, $Z^{10}$ and $Z^{10'}$ are the same, and each represents a single heteroatom selected from the group consisting a sulfur atom, an oxygen atom, and an optionally substituted nitrogen atom. In another illustrative embodiment, at least one of $Z^{10}$ and $Z^{10'}$ has the formula —NQ-, at least one of $Z^{11}$ and $Z^{11'}$ is an arylene or alkylene group, and Q is an electron withdrawing group. In yet another illustrative embodiment, each of $Z^{10}$ and $Z^{10'}$ has the formula —NQ-, each of $Z^{11}$ and $Z^{11'}$ is an alkylene group, and Q is an electron withdrawing group. Although one of $Z^{10}$ and $Z^{11}$ and/or one of $Z^{10'}$ and $Z^{11'}$ can represent a direct bond between the carbons to which they are attached, this need not be the case, for example as when only three, only two, only one, or none of $Z^{10}$, $Z^{11}$, $Z^{10'}$, and $Z^{11'}$ represents such a direct bond. $R^{78}$, $R^{78'}$, $R^{79}$, and $R^{79'}$ are independently selected from the group consisting of H, an alkyl group, and an aryl group, such as in the case where each of $R^{78}$, $R^{78'}$, $R^{79}$, and $R^{79'}$ represents a hydrogen. $Z^{12}$ represents an alkylene or arylene group, such as a substituted or unsubstituted 1,3-phenylene group.

As indicated in the formulae above, each of the two carboxylate groups includes a first carboxylate oxygen atom ("$O^1$"), a second carboxylate oxygen atom ("$O^2$"), and a carbon ("C") to which the $O^1$ and the $O^2$ are bonded thereby forming two $O^1$—C—$O^2$ moieties. $O^1$ of each of the two carboxylate groups of each of the two carboxylate ligands is bonded to the first rhodium ($Rh^1$); $O^2$ of each of the two carboxylate groups of each of the two carboxylate ligands is bonded to the second rhodium ($Rh^2$).

Each of the two carboxylate ligands further includes at least two stereocenters. These stereocenters, for example, can be included in one or more of $Z^{10}$, $Z^{11}$, $Z^{10'}$, and $Z^{11'}$, and/or they can be located at the carbon atoms to which $Z^{10}$, $Z^{11}$, $Z^{10'}$, and $Z^{11'}$ are bonded. The stereochemistry at these stereocenters are selected such that the catalyst, taken as a whole, has $D_2$ symmetry.

Illustrative examples of such dirhodium tetracarboxylate catalysts include those having the formula ("Formula IV"):

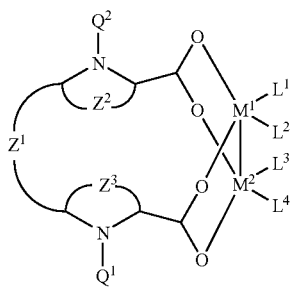

In Formula IV, $M^1$ and $M^2$ represent rhodium atoms or ions. $Z^2$ and $Z^3$, independently, are the atoms necessary to complete a 3–12 membered heterocyclic ring. Examples of such atoms include: substituted or unsubstituted alkylene moieties, such as those having the formula —$(CH_2)_i$—, where i is an integer from 1 to 8; and moieties having the formula —$(CH_2)_i$—X—$(CH_2)_j$—, where i and j each independently represent integers from 0 to 4 and X is a heteroatom, such as O, S, and $NR^{70}$, where $R^{70}$ is a substituted or unsubstituted alkyl, aryl, or heteroaryl group. Illustratively, $Z^2$ and $Z^3$ can be the same, as in the case where each of $Z^2$ and $Z^3$ has the formula —$CH_2CH_2$—. $Z^1$ is an alkylene or arylene group. Illustratively, $Z^1$ can have the formula —$(CH_2)_i$—, where i is an integer from 1 to 8. Alternatively, $Z^1$ can have the formula —$(CH_2)_i$—X—$(CH_2)_j$—, where i and j each independently represent integers from 0 to 4 and X is a heteroatom, such as O, S, and $NR^{70}$, where $R^{70}$ is an alkyl or aryl group. Still alternatively, $Z^1$ can be a cycloalkyl moiety, such as cyclopent-1,3-diyl and cyclohex-1,3-diyl, which can be substituted or unsubstituted. Still alternatively, $Z^1$ can be an arylene moiety, such as a 1,3-phenylene or 1,3-naphthylene, or an heterocyclic moiety, such as a pyrid-3,5-diyl, pyrid-2,6-diyl, 2H-pyran-3,5-diyl, and tetrohydropyran-3,5-diyl moiety. $Q^1$ and $Q^2$ are the same or different and are electron withdrawing groups. Examples of $Q^1$ suitable for use in the practice of the present invention are moieties having the formulae —$C(O)R^1$, —$SO_2R^1$, and —$P(O)R^1R^{1'}$, and examples of suitable $Q^2$ include moieties having the formulae —$C(O)R^2$, —$SO_2R^2$, and —$P(O)R^2R^{2'}$. In these formulae, each of $R^1$, $R^{1'}$, $R^2$, and $R^{2'}$ is independently selected from an alkyl group, an aryl group, and an alkoxy group. In one illustrative embodiment, $Q^1$ has the formula —$SO_2R^1$; $Q^2$ has the formula —$SO_2R^2$; and $R^1$ and $R^2$ are the same or different and are substituted or unsubstituted alkyl or aryl groups, such as in the case where $Q^1$ has the formula —$SO_2R^1$; $Q^2$ has the formula —$SO_2R^2$; and each of $R^1$ and $R^2$ is independently selected from the group consisting of 4-(t-butyl)phenyl, 2,4,6-trimethylphenyl, and 2,4,6-triisopropylphenyl. In the above Formula IV, $L^1$ and $L^3$, taken together, represent a —O—$CR^{13}$—O— moiety, and $L^2$ and $L^4$, taken together, represent a —O—$CR^{14}$—O— moiety. In these moieties, $R^{13}$ and $R^{14}$ can be the same or they can be different, and each is independently selected from the group consisting of alkyl groups and aryl groups. Alternatively, $R^{13}$ and $R^{14}$ can represent alkylene or arylene groups that are directly or indirectly bonded to one another. In the latter case, the dirhodium tetracarboxylate catalysts of Formula IV can be expressed as the following formula ("Formula V"):

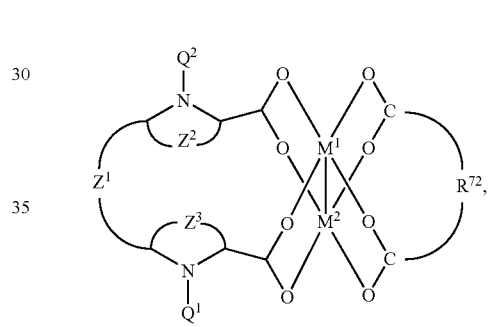

where $R^{72}$ represents an alkylene or arylene group. Illustratively, $R^{72}$ can be selected such that the dirhodium tetracarboxylate catalysts of Formula V have the following formula ("Formula VI"):

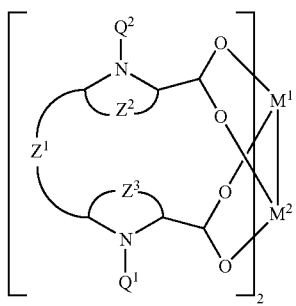

The dirhodium tetracarboxylate catalysts of Formulae IV, V, and VI have at least four stereocenters (i.e., at least the two carbons to which $Z^2$ is bonded and at least the two carbons to which $Z^3$ is bonded are stereocenters). Formulae IV, V, and VI are not meant to be limited to any particular set of configurations at the catalyst's stereocenters, and the structures given in these formulae are meant to be broadly read to include any and all possible collections of stereocenters. For example, catalysts of Formula VI are meant to include (i) compounds having the formula ("Formula VII"):

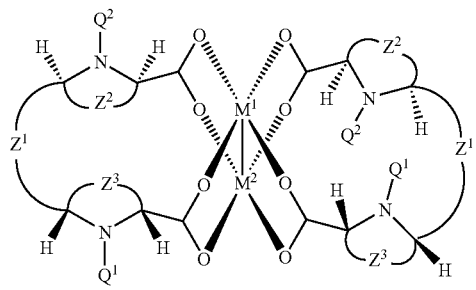

and (ii) compounds having the formula ("Formula VIII"):

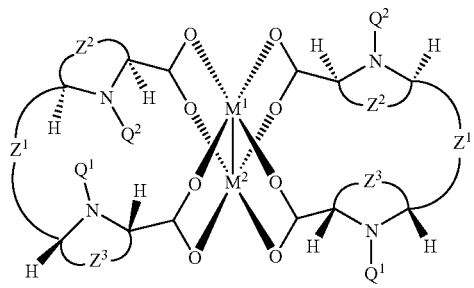

Each of the catalysts having Formulae VII and VIII can be present alone (i.e., as a pure diastereoisomer), or it can be present in a mixture with one or more different diastereoisomers. Alternatively, the catalysts having Formulae VII and VIII can be substantially free of other diastereoisomers. In this context, "substantially free of other disatereoisomers" means that the molar ratio of other diastereoisomers to the catalyst is less than 40%, such as less than 30%, less than 20%, less than 10%, less than 5%, less than 2%, and/or less than 1%.

Examples of catalysts having Formula VII and VIII, respectively, are those having the formula ("Formula IX"):

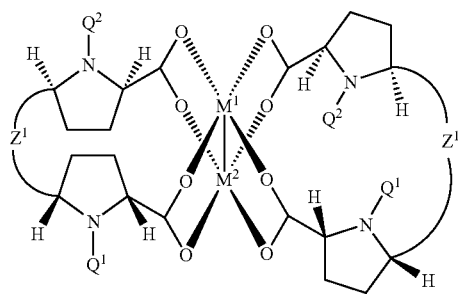

and those having the formula ("Formula X"):

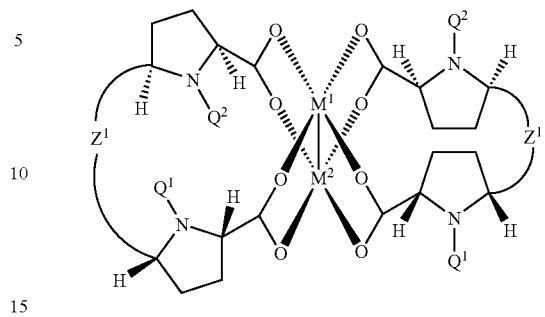

Still other examples of catalysts having Formula VII and VIII, respectively, are those having the formula ("Formula XI"):

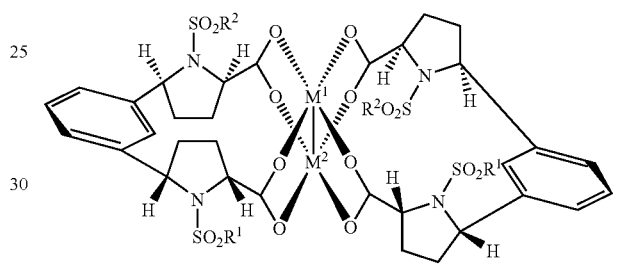

and those having the formula ("Formula XII"):

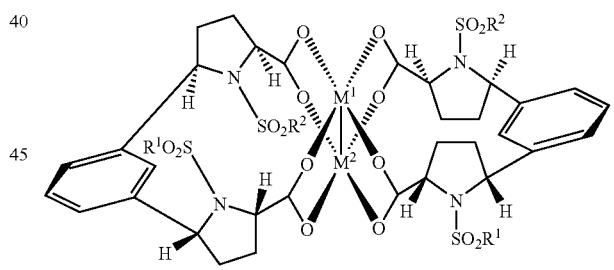

In Formula XI and Formula XII, $R^1$ and $R^2$ can be the same or different and each can be selected from, for example, alkyl groups and aryl groups.

As used in the above discussion and elsewhere herein, "arylene" is meant to include a bivalent aryl group in which both valencies are present on aromatic carbons. Examples of such groups include, for example, 1,3-phenylene, 1,4-phenylene, 5-methyl-1,3-phenylene, pyrid-2,3-diyl, pyrid-2,4-diyl, pyrid-2,5-diyl, pyrid-3,5-diyl, 1,3-naphthylene, 1,7-naphthylene, 1,8-naphthylene, 5,6,7,8-tetrahydro-1,3-naphthylene, thiophene-2,5-diyl, and furan-2,5-diyl. "Arylene", as used herein, is also meant to include a bivalent group having the formula —R—R'—, where R is an alkyl group and R' is an aryl group. As the structure of —R—R'— indicates, one of the valencies is on the R (i.e., alkyl) portion of the —R—R'— moiety and the other of the valencies resides on the R' (i.e., aryl) portion of the —R—R'— moiety. Examples of this type of arylene moiety include moieties having the formulae:

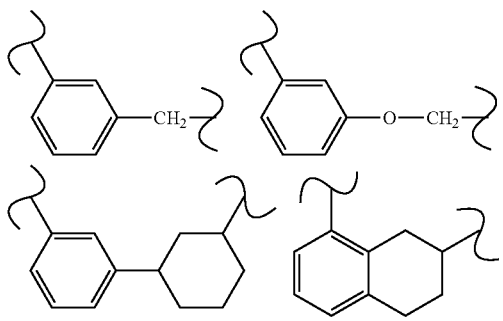

and the like.

Other suitable dirhodium tetracarboxylate catalysts as well as methods for making various dirhodium tetracarboxylate catalysts are described in, for example, U.S. Pat. No. 6,410,746 to Davies, International Publication No. WO 00/64583; and Davies et al., "Novel Dirhodium Tetraprolinate Catalysts Containing Bridging Prolinate Ligands For Asymmetric Carbenoid Reactions," *Tetrahedron Letters*, pages 5287–5290 (1999), each of which is hereby incorporated by reference.

Other suitable dirhodium catalysts include dirhodium tetracarboxamidate catalysts, such as those having the following formula ("Formula XIII"):

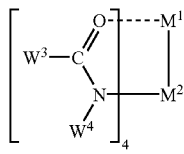

In Formula XIII, each of $M^1$ and $M^2$ is Rh. $W^3$ represents an alkyl group, an aryl group, an alkoxy group, or an amine group, and $W^4$ represents an alkyl group or an aryl group. Alternatively, $W^3$ and $W^4$, taken together with the atoms to which they are bonded, represent a 3–12 membered ring, for example, as shown in the following formula ("Formula XIV"):

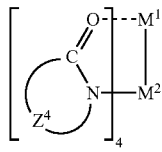

In Formula XIV, $Z^4$ represents the atoms necessary to complete a 3–12 membered ring. The ring can be substituted or unsubstituted; and it can include additional heteroatoms (i.e., in addition to the N to which $Z^4$ is bonded, or it can consist only of carbons (except for the N to which $Z^4$ is bonded). Illustratively, $Z^4$, together with the carbon and N atoms to which it is bonded, can represents a substituted or unsubstituted C3–C8 lactam ring, a substituted or unsubstituted oxazolidone ring, a substituted or unsubstituted pyrrolidone ring, or a substituted or unsubstituted imidazolidone ring. Specific examples of suitable catalysts of Formula XIV include: dirhodium(II) tetrakis(caprolactam); dirhodium(II) tetrakis[methyl 2-oxazolidone-4-carboxylate]; dirhodium(II) tetrakis[methyl 2-oxazolidone-4-(S)-carboxylate]; dirhodium(II) tetrakis[methyl 2-pyrrolidone-5-carboxylate]; dirhodium(II) tetrakis[methyl 2-pyrrolidone-5(R)-carboxylate]; dirhodium(II) tetrakis[methyl 2-pyrrolidone-5(S)-carboxylate]; dirhodium(II) tetrakis [methyl 1-(3-phenylpropanoyl)-2-imidazolidone-4-carboxylate]; dirhodium(II) tetrakis[methyl 1-(3-phenylpropanoyl)-2-imidazolidone-4(S)-carboxylate; and adducts (e.g., acetonitrile and/or alcohol adducts) thereof. Methods for producing these and other dirhodium tetracarboxamidate catalysts can be found, for example, in U.S. Pat. No. 5,175,311 to Doyle, which is hereby incorporated by reference.

The aforementioned dirhodium catalysts and organic esters can be provided neat (i.e., in the absence substantially all other materials) or either the dirhodium catalyst or the organic esters or both can be provided as a mixture with other materials, such as, for example, solvents, reactants, and the like. Where the dirhodium catalysts and organic esters are provided in solution form, they can be provided in concentrated form (e.g., at a concentration greater than about 5 times the concentration at which they will be used in the catalytic reaction) or they can be provided in dilute form (e.g., at a concentration less than about 5 times the concentration at which they will be used in the catalytic reaction). Where solvents are employed, it is desirable that the solvent used to dissolve or suspend the organic ester and the solvent used to dissolve or suspend the dirhodium catalyst be miscible with one another or miscible with the solvent in which the catalytic reaction is to be carried out. The choice of solvent(s), of course, will depend on a number of factors including miscibility of the organic ester and/or dirhodium catalyst in the solvent(s), possible side reactions between the solvent(s) and the organic ester, the dirhodium catalyst, and other materials to be present during the catalytic reaction, difficulty of separating product from the solvent(s), difficulty in drying the solvent (in cases where dry solvent is needed), boiling point and/or decomposition point of the solvent relative to the temperature at which the catalytic is to be carried out, cost considerations, disposal considerations, and the like. Suitable solvents include, for example, hydrocarbon solvents (e.g., hexanes and cyclohexane) and chlorinated hydrocarbons (e.g., chloroform and methylene chloride), as well as aromatic solvents (e.g., toluene and xylenes).

Once the dirhodium catalysts and organic esters are provided, they are then contacted with one another under conditions effective to increase the catalyst's efficiency (e.g., to increase the catalyst's turnover number and/or turnover rate). This contact can take place at any time prior to or during the catalytic reaction. Illustratively, the dirhodium catalyst and organic ester can be contacted with one another prior to being mixed with the reactant(s) to be catalyzed. Alternatively, the dirhodium catalyst can be premixed with the reactant(s) and then this mixture can be contacted with the organic ester. Still alternatively, the organic ester can be premixed with the reactant (s), and then this mixture can be contacted with the dirhodium catalyst. Still alternatively, the organic ester can be premixed with a portion of the reactants and the dirhodium catalyst can be premixed with the remainder of the reactants and then this mixture can be contacted with the dirhodium catalyst, and then the two mixtures can be mixed together, thus contacting the dirhodium catalyst and organic ester with one another.

It should be understood that where the present application recites a 2-step process of (i) providing a composition containing dirhodium catalyst ("DC") and organic ester ("OE") and (ii) contacting this composition with some other material ("OM"), such as a reactant, step (i) can be performed first (e.g., by mixing DC and OE with each other) and then, in a separate step (ii), contacting the mixture with OM. Alternatively, steps (i) and (ii) can be performed simultaneously, for example, by first mixing DC and OM and then contacting the DC/OM mixture with OE; by first mixing OE and OM and then contacting the OE/OM mixture with DC; or by adding OE and DM separately but simultaneously to OM.

In one embodiment of the present invention, the dirhodium catalyst and the organic ester are brought into contact with one another either prior to commencement of the reaction (e.g., prior to contacting the catalyst with the reactant(s)) or shortly after the reaction has begun (e.g., before more than half of the expected yield of product is produced). Although contacting the dirhodium catalyst and the organic ester with one another late in the reaction (e.g., after more than half of the expected yield of product is produced) is not optimal, such a practice can, nevertheless, be effective to increase the efficiency of the dirhodium catalyst for the latter portion of the reaction and, thus, for the overall reaction.

The dirhodium catalyst and the organic ester are contacted with one another such that the dirhodium catalyst and the organic ester are present in a molar ratio effective to increase the efficiency (e.g., the turnover number and/or the turnover rate) of the dirhodium catalyst, such as by more than a measurable amount, such as by more than about 0.5%, by more than about than about 1%, by more than about 5%, by more than about 10%, by more than about 50%, by more than about 100%, by more than about 1000%, by more than about 9000%, and/or by more than about 100000%. Suitable organic ester:dirhodium catalyst mole ratios include mole ratios of from about 0.01:1 to about $10^8$:1, such as from about 0.1:1 to about $10^7$:1, from about 1:1 to about $10^6$:1, from about 10:1 to about $10^5$:1, from about 100:1 to about $10^4$:1, from about 100:1 to about $10^6$:1, and/or from about 1000:1 to about $10^6$:1. Conveniently, the number moles of organic ester employed can be equal to the number of moles of the limiting reactant present in the reaction to be catalyzed with the dirhodium catalyst.

The dirhodium catalyst will generally never serve as a solvent for the organic ester. In some circumstances, the organic ester can serve as a solvent for the dirhodium catalyst or for the reaction to be catalyzed. Typically, however, even in cases where the organic ester can serve as a solvent for the dirhodium catalyst or for the reaction to be catalyzed, the reaction will be carried out either in an inert solvent or in a solvent which also serves as one of the reactants and the mole ratio of this inert solvent or reactant/solvent to the organic ester can be typically be greater than 1, such as greater than 2, greater than 3, and/or greater than 5.

In one embodiment of the present invention, the reaction is carried out in the presence of a suitable drying agent, such as molecular sieves, sodium sulfate, magnesium sulfate, calcium sulfate, and the like.

The present invention also relates to compositions which include a dirhodium catalyst and an organic ester, in which the organic ester is selected such that it is not a substrate for catalysis by the dirhodium catalyst. Suitable dirhodium catalysts, organic esters, molar ratios, etc. include those described above in relation to the method of the present invention. The composition can include only the dirhodium catalyst and organic ester, or it can include other materials, such as solvents, dispersants, reactants, drying agents (e.g., molecular sieves), and the like. Thus, the composition of the present invention encompasses a mixture of dirhodium catalyst/organic ester prior to its being brought into contact with the reactant(s) as well as after its being brought into contact with the reactants. In cases where the dirhodium catalyst component and organic ester component are added separately to the reactant(s), the composition of the present invention forms in situ upon addition of the last-to-be-added component. Once formed, the composition of the present invention typically continues to exist until all of the dirhodium catalyst component is separated from all of the organic ester component or until all of one or the other component is consumed or destroyed, whichever comes first.

The method of the present invention and the composition of the present invention can be used in a variety of dirhodium catalyzed reactions. Briefly, these include: insertion reactions (which are meant to include C—H insertions, Si—H insertions, O—H insertions, and N—H insertions), cyclopropanation reactions, annulations (which are meant to include [3+2] annulations and [3+4] annulations), and ω,ω-diarylalkanoate syntheses.

For example, the method and composition of the present invention can be used in a variety of insertion reactions. One such insertion reaction relates to a method for producing a compound having the formula ("Formula XV"):

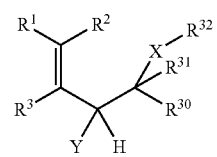

$R^1$, $R^2$, and $R^3$ are independently selected from H, alkyl, aryl, or vinyl, or $R^1$ and $R^3$, together with the atoms to which they are bonded, form a 5–12 membered ring, such as a cyclohexene ring, or a cyclohexa-1,3-diene ring. The method can be used to prepare compounds in which $R^1$ and $R^3$, together with the atoms to which they are bonded, form an aromatic ring, such as a substituted or unsubstituted phenyl ring, pyridine ring, thiophene ring, indole ring, etc. In the case where $R^1$ and $R^3$, together with the atoms to which they are bonded, form a phenyl ring, the compound produced by this method can have the formula ("Formula XVI"):

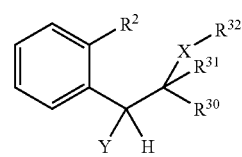

Y is an electron withdrawing group, examples of which include moieties having the formulae: —C(O)$R^{77}$, —SO$_2$$R^{77}$, and —P(O)$R^{77}$$R^{77'}$. In these formulae, each of $R^{77}$ and $R^{77'}$ is independently selected from an alkyl group, an aryl group, and an alkoxy group. Illustratively, Y can have the formula $CO_2R^{12}$ where $R^{12}$ is an alkyl group or an aryl group.

X is $CH_2$, O or $NR^{11}$, and $R^{11}$ is H, an alkyl group, an aryl group, an acyl group, an alkoxycarbonyl group, or a silyl group having the formula $-SiR^{33}R^{34}R^{35}$, where $R^{33}$, $R^{34}$, and $R^{35}$ are independently selected from an alkyl group and an aryl group.

Each of $R^{30}$ and $R^{31}$ is independently selected from the group consisting of H, alkyl, aryl, and vinyl. $R^{32}$ is an alkyl group, an aryl group, an acyl group, an alkoxycarbonyl group, or a silyl group having the formula $-SiR^{36}R^{37}R^{38}$, where $R^{36}$, $R^{37}$, and $R^{38}$ are independently selected from an alkyl group and an aryl group. Alternatively, $R^{31}$ and $R^{32}$, together with the atoms to which they are bonded, can form a 5–12 membered ring, such as a cyclopentyl or cyclohexyl ring (in the case where X is $-CH_2-$), a piperidinyl ring (in the case where X is N), or a tetrahydrofuranyl or a tetrahydropyranyl ring (in the case where X is O). Illustratively, this method is well-suited for forming compounds having Formula XV in which X is not $CH_2$ when each of $R^{30}$ and $R^{31}$ is H.

The method includes providing a diazo compound having the formula ("Formula XVII"):

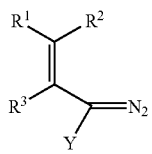

in which $R^1$, $R^2$, $R^3$, and Y have the same meanings as given above with reference to Formula XV. The method further includes converting the diazo compound with a compound having the formula ("Formula XVIII"):

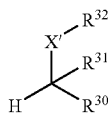

in the presence of a dirhodium catalyst composition of the present invention and under conditions effective to produce the compound. In compound XVIII, $R^{30}$, $R^{31}$, and $R^{32}$ are defined as they are above with regard to Formula XV. When, in the desired product, X is $CH_2$ or O, X' in Formula XVIII is $CH_2$ or O, respectively. When, in the desired product, X is $NR^{11}$, X' in Formula XVIII is $NR^{11'}$ and $R^{11'}$ is an alkyl group, an aryl group, an acyl group, an alkoxycarbonyl group (e.g., BOC or another alkoxycarbonyl amine protecting group), or a silyl group (e.g., a triarylsilyl group, or a trialkylsilyl group).

Suitable dirhodium catalysts for carrying out the conversion of XVII with XVIII are those having Formulae I–II and IV–XIV, as defined and discussed above. Other suitable dirhodium catalysts for carrying out the conversion of XVII with XVIII are chiral dirhodium catalysts, such as those having $D_2$ symmetry, for example, those which include a two rhodium atoms or ions that are bonded to one another along an axis and two carboxylate ligands, each of which two carboxylate ligands includes two carboxylate groups bonded to each other via a moiety having Formula III. Such dirhodium catalysts are discussed in greater detail above.

Illustratively, the reaction can be carried out by mixing the catalyst and organic ester (e.g., methyl benzoate) with the compound of Formula XVIII. In the case where the compound of Formula XVIII is a liquid (e.g., in the case where the compound of Formula XVIII is tetrahydrofuran, tetrahydropyran, N-(tert-butyloxycarbonyl)pyrrolidine, N-(tert-butyloxycarbonyl)piperidine, cyclopentane, cyclohexane, etc.), this can be effected without the use of additional solvent. Alternatively, the mixture can be formed using an inert solvent or a solvent which is significantly less reactive toward the diazo compound of Formula XVII than is the compound of Formula XVIII. As an example, it has been found that when the compound of Formula XVIII is tetrahydrofuran, the catalyst, organic ester, and tetrahydrofuran can be mixed neat (i.e., using tetrahydrofuran as the solvent and without the use of additional solvent), or hexanes can be used as a reaction medium. The amount of catalyst used in this reaction can be between one-half and $\frac{1}{1000}$th that which would be employed in the absence of the organic ester. For example, suitable mole ratios of the catalyst to the diazo compound of Formula XVII are: from about $1:10^8$ to about 1:50, such as from about $1:10^7$ to about 1:100, from about $1:10^6$ to about 1:10,000, from about $1:10^8$ to about $1:10^7$, from about $1:10^8$ to about $1:10^6$, from about $1:10^8$ to about $1:10^5$, and/or from about $1:10^8$ to about $1:10^4$. Illustratively, the dirhodium catalyst and the diazo compound can be present in a mole ratio of greater than 2000:1, such as greater than about 5000:1, greater than about $10^4:1$, and/or greater than about $10^4:1$. Suitable organic ester: dirhodium catalyst mole ratios include mole ratios of from about 0.01:1 to about $10^8:1$, such as from about 0.1:1 to about $10^7:1$, from about 1:1 to about $10^6:1$, from about 10:1 to about $10^6:1$, from about 100:1 to about $10^4;1$, from about 100:1 to about $10^6:1$, and/or from about 1000:1 to about $10^6:1$.

Once the catalyst, organic ester, and compound of Formula XVIII are mixed, the diazo compound of Formula XVII is added, for example with stirring. This addition can be carried out in a single portion, continuously, or batchwise. Slow, dropwise addition can be effected, for example, using a syringe pump. The amount of diazo compound of Formula XVII added is generally dependent on the amount of the compound of Formula XVIII present in the reaction mixture. Illustratively, the mole ratio of the compound of Formula XVIII to the diazo compound of Formula XVII is from about 1:10 to about 10:1, such as from about 6:1 to about 1:1 and/or from about 4:1 to about 2:1. The addition can be carried out at any suitable temperature from the freezing point to the boiling point of, the solvent and/or the compound of Formula XVIII. For example, the addition can be carried out from about −50° C. to about 60° C. Room temperature addition and addition at about 10° C. are illustrative. Illustratively, in one embodiment of the present invention where diastereomerically and/or enantiomerically pure product is desired, reaction conditions can be optimized by adjusting the addition temperature. Although not intending to be limitative in any way on the scope of the present invention, it is believed that (i) formation of diastereomerically and/or enantiomerically pure product can be favored by lower addition temperatures (e.g., from about −50° C. to about 10° C.); and (ii) yield and improved diastereoisomeric and/or enantiomeric purity can be improved by performing the reaction substantially in the absence of oxygen. As used herein, "substantially in the absence of oxygen" means that the liquid reactants and solvents (if any) employed in carrying out the reaction are degassed, for example by bubbling an inert gas (e.g., nitrogen or argon) therethrough, that the reaction is carried out under blanket of inert gas, and that all transfers (subsequent to degassing) are carried out such that ambient air is excluded (e.g., by using rubber septums, gas tight syringes, and the like).

The conversion of the compound of Formula XVII with a compound of Formula XVIII to produce either or both diastereomers of a compound of Formula XV described above can be used for preparing compounds having the formula ("Formula XIX"):

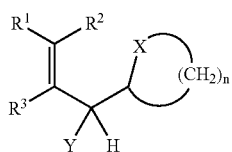

In this case, the conversion of the diazo compound of Formula XVII is carried out with a cyclic compound having the formula ("Formula XX"):

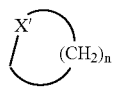

in which X' is defined as above and n is 3–10. In one illustrative embodiment, $R^1$ and $R^3$, together with the atoms to which they are bonded, form a phenyl ring, and Y has the formula —$CO_2R^{10}$ where $R^{10}$ is an alkyl or aryl group. The method can be used, for example, to make compounds in which X is $NR^{11}$ and in which n is 3 or 4. The method is also suitable for making compounds having the formulae ("Formula XXI-A" and "Formula XXI-B", respectively):

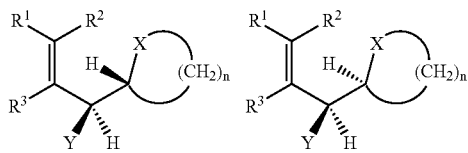

in which case the dirhodium catalyst employed is a chiral dirhodium catalyst. For example, by using the S-isomer of compounds having Formulae IV–XII, as defined and discussed above, compounds of Formula XXI-B which are substantially enantiomerically pure (e.g., >80% ee, >90% ee, >95% ee, >98% ee, and/or >99% ee) can be prepared. Examples of compounds having Formula XXI-A and XXI-B include those in which X is $NR^{11}$, n is 3 or 4, Y is $CO_2R^{12}$, $R^{12}$ is alkyl or aryl, and $R^1$ and $R^3$, together with the atoms to which they are bonded, form an aromatic ring, such as those compounds of Formulae XXI-A or XXI-B in which X is NH, $R^{12}$ is a methyl group, and $R^1$ and $R^3$, together with the atoms to which they are bonded, form a phenyl ring. Such compounds can have one of the following formulae ("Formula XXII-A" and "Formula XXII-B", respectively):

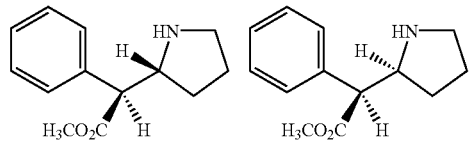

or one of the following formulae ("Formula XXII-C" and "Formula XXII-D", respectively):

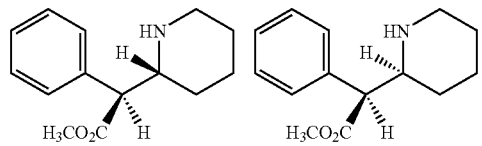

the latter of which is also referred to as threo methylphenidate and which is believed to be the biologically active form of RITALIN™. Where stereospecifcity is not important, racemic mixtures of compounds having Formulae IV–XII or other dirhodium tetracarboxylates can be employed in the method and/or composition of the present invention to produce the racemic methylphenidate.

The method of the present invention can also be used to prepare compounds having Formula XV in which X is $NR^{11}$ and in which $R^{31}$ and $R^{32}$, together with the atoms to which they are bonded, represent a ring having the formula ("Formula XXIII"):

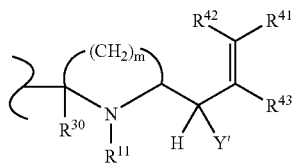

where $R^{30}$ is H. That is, the method can be used to prepare compounds having the formula ("Formula XXIV"):

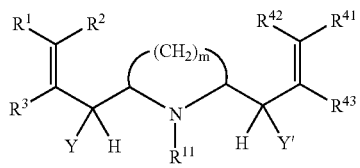

In these formulae, $R^{41}$, $R^{42}$, and $R^{43}$ are independently selected from H, alkyl, aryl, or vinyl, or $R^{41}$ and $R^{43}$, together with the atoms to which they are bonded, form a 5–12 membered ring. Y' is an electron withdrawing group, for example, the electron withdrawing groups discussed above with regard to Y, and m is 2–9. The reaction involves providing a diazo compound having Formula XVII and converting the diazo compound with a cyclic amine having the formula ("Formula XXV"):

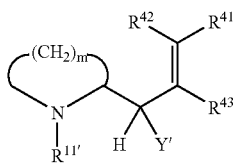

in the presence of a dirhodium catalyst composition of the present invention and under conditions effective to produce the compound. Suitable conditions for this reaction are the same as the ones discussed above with regard to the conversion of compounds of Formula XVII with compounds of Formula XVIII. By using a chiral catalyst, compounds having the formula ("Formula XXVI"):

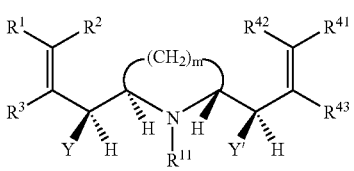

can be produced.

A variety of methods can be used to prepare the cyclic amine having Formula XXV, such as the method that is described above with regard to preparing compounds having Formula XIX using diazo compounds of Formula XVII, cyclic compounds of Formula XX, and a dirhodium catalyst composition of the present invention. Rather than running the reaction in two steps (i.e., by first reacting a diazo compounds of Formula XVII with a cyclic compound of Formula XX in which X is N to produce a cyclic amine having Formula XIX and then reacting the cyclic amine having Formula XIX with a diazo compound having Formula XVII to produce the desired compound of Formula XXIV), the reaction can be carried out in a single step, for example, by contacting the cyclic compound of Formula XX in which X is N with at least two equivalents of a diazo compound of Formula XVII. Reaction conditions suitable for carrying out this one step transformation include those discussed above with regard to the two step method. It will be understood that the "one step" and "two step" labels assigned to the above methods are only for brevity and that these methods can, optionally, further additional steps (e.g., a second, third, fourth, etc. step in a one step method; and a third, fourth, etc. step on a two step method). Illustratively, during the first part of the reaction (i.e., during the addition of the first half of the diazo compound having Formula XVII), the reaction is carried out with cooling (e.g., from about −50° C. to about 0° C.). Then the reaction mixture is warmed, and the second part of the reaction (i.e., during the addition of the second half of the diazo compound having Formula XVII) is carried out at elevated temperatures (e.g., from about 20° C. to about 100° C.). Alkanes having melting points of less than about −50° C. and boiling points greater than about 60° C. are the suitable solvents for this reaction, but the nature of the solvent is not particularly critical and alternatives can be used.

The compounds prepared by the above method (i.e., compounds having Formulae XV, XVI, XIX, XXI-A, XXI-B, XXII-A, XXII-B, XXII-C, XXII-D, XXIV, and XXVI) are appropriately functionalized for further conversion by, for example, ester reduction or Grignard addition to highly functionalized bases. In the case where a chiral catalyst is employed, e.g., the S-isomer of compounds having Formulae IV–XII, as defined and discussed above, these compounds can be used as $C_2$ symmetric bases, or, as indicated above, they can be further converted (e.g., by ester reduction or Grignard addition) to highly functionalized $C_2$ bases. $C_2$ bases are very useful for controlling stereochemistry in organic synthesis, for example, as described in Takahata et al., "New Entry to C2 Symmetric Trans-2,6-bis(hydroxymethyl)piperidine Derivatives Via the Sharpless Asymmetric Dihydroxylation," *Tetrahedron-Asymmetry*, 6:1085–1088 (1995) and in Bennani et al., "Trans-1,2-diaminocyclohexane Derivatives as Chiral Reagents, Scaffolds, and Ligands for Catalysis—Applications in Asymmetric Synthesis and Molecular Recognition," *Chemical Reviews*, 97:3161–3195 (1997), which are hereby incorporated by reference.

Further examples and details of using dirhodium catalysts to effect insertions can be found, for example, in Davies et al., "Catalytic Asymmetric C—H Activation of Silyl Enol Ethers as an Equivalent of an Asymmetric Michael Reaction," *J. Am. Chem. Soc.*, 123(9):2070–2071 (2001); Davies et al., "Kinetic Resolution and Double Stereodifferentiation in Catalytic Asymmetric C—H Activation of 2-Substituted Pyrrolidines," *Organic Letters*, 3(11):1773–1775 (2001); Davies et al., "Asymmetric Intramolecular C—H Insertions of Aryldiazoacetates," *Organic Letters*, 3(10):1475–1477 (2001); Catalytic Asymmetric C—H Activation of Alkanes and Tetrahydrofuran," *J. Am. Chem. Soc.*, 122(13):3063–3070 (2000); Davies et al., "Highly Regio-, Diastereo-, and Enantioselective C—H Insertions of Methyl Aryldiazoacetates into Cyclic N-Boc-Protected Amines. Asymmetric Synthesis of Novel $C_2$-Symmetric Amines and threo-Methylphenidate," *J. Am. Chem Soc.*, 121(27):6509–6510 (1999); Davies et al., "Catalytic Asymmetric Synthesis of Syn-Aldol Products from Intermolecular C—H Insertions Between Allyl Silyl Ethers and Methyl Aryldiazoacetates," *Organic Letters*, 1(3):383–385 (1999); Davies, "Rhodium-Stabilized Vinylcarbenoid Intermediates in Organic Synthesis," *Current Organic Chemistry*, 2:463–488 (1998); Davies et al., "Recent Progress in Asymmetric Intermolecular C—H Activation by Rhodium Carbenoid Intermediates," *Journal of Organometallic Chemistry*, 617–618:47–55 (2001); Davies, "Dirhodium Tetra(N-arylsulfonylprolinates) as Chiral Catalysts For Asymmetric Transformations of Vinyl- and Aryldiazoacetates," *Eur. J. Org. Chem.*, pages 2459–2469 (1999); Davies, "Asymmetric Synthesis Using Rhodium-Stabilized Vinylcarbenoid Intermediates," *Aldrichimica Acta*, 30(4):107–114 (1997); U.S. Pat. No. 6,410,746 to Davies; and International Publication No. WO 00/64583. Collectively, these references are referred to herein as the "Insertion References", and each of these references is hereby incorporated by reference. The reactions set forth in the Insertion References and other references relating to dirhodium catalyzed insertion reactions can be carried out using the dirhodium catalyst composition of the present invention in place of the dirhodium catalysts described in the Insertion References. The dirhodium catalyst composition of the present invention can contain between one-half and 1/1000th of the amount of dirhodium called for in the Insertion References, and the dirhodium catalyst composition of the present invention further contains an organic ester, for example, of the type and amounts specified hereinabove.

The method and composition of the present invention can also be used in connection with other insertion reactions, as well as with cyclopropanation reactions. Such other insertion reactions and such cyclopropanation reactions are illustrated by the following method for producing a compound having the formula ("Formula XXVII"):

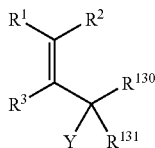

In Formula XXVII, $R^1$, $R^2$, and $R^3$ are independently selected from H, alkyl, aryl, or vinyl, or $R^1$ and $R^3$, together with the atoms to which they are bonded, form a 5–12 membered ring. Y is an electron withdrawing group (e.g., an ester group). $R^{131}$ is H, and $R^{130}$ is an alkyl group, an aryl group, an alkoxy group, an amine group, or a silyl group; or $R^{130}$ and $R^{131}$, together with the atom to which they are bonded, form a substituted or unsubstituted cyclopropane moiety. The method includes providing a diazo compound having the formula ("Formula XXVIII"):

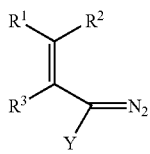

(in which $R^1$, $R^2$, $R^3$, and Y are defined as they are above with regard to Formula XXVII) and converting the diazo compound of Formula XXVIII to the compound of Formula XXVII in the presence of a dirhodium catalyst composition of the present invention and under conditions effective to produce the compound of Formula CII.

In cases where $R^{131}$ is H, and $R^{130}$ is an alkyl group, an aryl group, an alkoxy group, an amine group, or a silyl group, this reaction is a C—H, C—O, C—N, or C—Si insertion, and suitable reactants for effecting the conversion of the diazo compound of Formula XXVIII to the compound of Formula XXVII can be readily ascertained by one skilled in the art. Examples of such reactions are set forth in the Insertion References, and each of these references is hereby incorporated by reference. The reactions set forth in the Insertion References and other references relating to dirhodium catalyzed insertion reactions can be carried out using the dirhodium catalyst composition of the present invention in place of the dirhodium catalysts described in the Insertion References. To carry out the C—H, C—O, C—N, or C—Si insertion reactions represented by the conversion of the diazo compound of Formula XXVIII to the compound of Formula XXVII, the dirhodium catalyst composition of the present invention can contain between one-half and 1/1000th of the amount of dirhodium called for in the Insertion References, and the dirhodium catalyst composition of the present invention further contains an organic ester, for example, of the type and amounts specified hereinabove.

The above-described insertion reactions exemplify the present invention's usefulness in catalyzing aryldiazomethane or vinyldiazomethane insertion reactions in which aryldiazomethanes or vinyldiazomethanes are contacted with a dirhodium catalyst composition according to the present invention under conditions effective to catalyze the aryldiazomethane or vinyldiazomethane insertion reaction.

These methods provide new and useful ways to make compounds (such as the compounds illustrated by Formulae XV, XVI, XIX, XXI-A, XXI-B, XXII-A, XXII-B, XXII-C, XXII-D, XXIV, XXVI, and XXVII (in cases where $R^{131}$ is H)) and to produce C—H bonds.

In cases where $R^{130}$ and $R^{131}$, together with the atom to which they are bonded, form a substituted or unsubstituted cyclopropane moiety, the compound of Formula XXVII can have the formula ("Formula XXIX"):

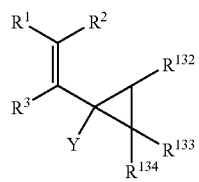

Such reactions are commonly referred to as cyclopropanation reactions. In Formula XXIX, each of $R^{132}$, $R^{133}$, and $R^{134}$ can independently represent H, an alkyl group, an aryl group, a silyloxy group, an alkoxy group, a halogen, an amine group, or an alkyl or aryl thiol group. Alternatively, $R^{132}$ and $R^{133}$, together with the atoms to which they are bonded, can form a 4–12 membered ring. Still alternatively, $R^{133}$ and $R^{134}$, together with the atom to which they are bonded, can form a 3–12 membered ring. Compounds of Formula XXIX can be produced by converting the diazo compound of Formula XXVIII using a compound having the formula ("Formula XXX"):

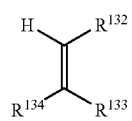

in which $R^{132}$, $R^{133}$, and $R^{134}$ are defined as they are above with regard to Formula XXIX. The reaction is carried out using a dirhodium catalyst composition of the present invention. Other reaction conditions suitable for carrying out this conversion are the same as those discussed above with regard to insertion reactions. The amount of catalyst used in this reaction can be between one-half and 1/1000th that which would be employed in the absence of the organic ester. For example, suitable mole ratios of the catalyst to the diazo compound of Formula XXVIII are: from about $1:10^8$ to about 1:50, such as from about $1:10^7$ to about 1:100, from about $1:10^6$ to about 1:10,000, from about $1:10^8$ to about $1:10^7$, from about $1:10^8$ to about $1:10^6$, from about $1:10^8$ to about $1:10^5$, and/or from about $1:10^8$ to about $1:10^4$. Illustratively, the dirhodium catalyst and the diazo compound can be present in a mole ratio of greater than 2000:1, such as greater than about 5000:1, greater than about $10^4:1$, and/or greater than about $10^4:1$. Suitable organic ester:dirhodium catalyst mole ratios include mole ratios of from about 0.01:1 to about $10^8:1$, such as from about 0.1:1 to about $10^7:1$, from about 1:1 to about $10^6:1$, from about 10:1 to about $10^5:1$, from about 100:1 to about $10^4:1$, from about 100:1 to about $10^6:1$, and/or from about 1000:1 to about $10^6:1$.

Once formed, compounds of Formula XXIX can be used in an number of ways.

For example, compounds of Formula XXIX in which at least one of $R^1$ and $R^2$ is H and in which $R^{132}$ is an electron donating group can be converted to cyclopentenes, for example, by treating the compound of Formula XXIX with a Lewis acid, such as diethyl aluminum chloride. As used herein, "electron donating group" refers to those groups which are able to inject electron density from adjacent positions in a molecule, as determined, for example, by reference to the classification established by the Hammett scale, such as the one set forth in Gordon, which is hereby incorporated by reference. Suitable electron-donating groups include those having a para a value less than or equal to about zero (e.g., less than or equal to about −1, and/or less than or equal to about −2 with reference to the Hammett scale. Particular examples of electron withdrawing groups are alkoxy groups.

Alternatively, compounds of Formula XXIX in which $R^1$ and $R^2$ are H, in which $R^{132}$ is an electron donating group (e.g., an alkoxy group), and in which $R^3$ is a silyloxy group can be converted to dihydrofurans, for example, by treating the compound of Formula XXIX with a fluoride, such as tetrabutylammonium fluoride.

Still alternatively, compounds of Formula XXIX in which at least one of $R^1$ and $R^2$ is H, in which $R^{132}$ is an electron donating group (e.g., an alkoxy group), in which Y is a carboxylic acid ester of the formula —$COOR^{160}$, and in which $R^{160}$ is a tertiary alkyl moiety (e.g., a t-butyl group) can be converted to butenolides, for example, by treating the compound of Formula XXIX with a Lewis acid catalyst, such a boron halide (e.g., $BF_3$ or $BBr_3$) or another Lewis acid catalyst containing boron.

Compounds of Formula XXIX can also be used to prepare compounds having the formula ("Formula XXXI"):

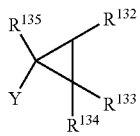

where each of $R^{132}$, $R^{133}$, $R^{134}$, and Y are defined as they were with regard to Formula XXIX and where $R^{135}$ is a carboxylic acid group, a carboxylic acid derivative (e.g., a carboxylic acid ester, a carboxylic acid amide, etc.), or an amino group (e.g., a unsubstituted, monosubstituted, or disubstituted amino group). The conversion of compounds of Formula XXIX to compounds of Formula XXXI in which $R^{135}$ is a carboxylic acid or carboxylic acid derivative can be effected, for example, by treating the compound of Formula XXIX with an oxidative alkene cleavage reagent, such as $RuCl_3/NaIO_4$. Compounds of Formula XXXI in which $R^{135}$ is a carboxylic acid or carboxylic acid derivative can be further converted to compounds of Formula XXXI in which $R^{135}$ is an amino group, for example by treatment with triethylamine, diphenylphosphoryl azide, and t-butyl alcohol; followed by treatment with di-t-butyl dicarbonate to produce a Boc-protected amine; and conversion of the Boc-protected amine to the free amine using, for example, strong acid (e.g., 3 N HCl in EtOAc). Using this method in conjunction with enantiomerically pure compounds of Formula XXIX (formed, for example, by using a dirhodium catalyst composition of the present invention containing a diastereomerically pure dirhodium catalyst), each of the four stereoisomers of 2-phenylcyclopropan-1-amino acid can be produced.

Compounds of Formula XXIX can also be converted to compounds having the formula ("Formula XXXII"):

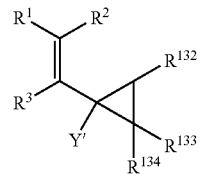

where each of $R^1$, $R^2$, $R^3$, $R^{132}$, $R^{133}$, and $R^{134}$ are defined as they were with regard to Formula XXIX and where Y' is an alkyl group, an aldehyde group, a ketone, or a vinyl group. As one illustrative example, $R^2$ can be H; $R^1$ and $R^3$, together with the atoms to which they are bonded, can form a phenyl group; $R^{132}$ can be H; $R^{133}$ can be a 4-alkoxyphenyl group; $R^{134}$ can be a phenyl group; Y can be a carboxylic acid ester; and Y' can be an aldehyde group, a hydroxymethyl group, a vinyl group, or an ethyl group. Compounds of Formula XXIX can be converted to a compound of Formula XXXII where Y' is a hydroxymethyl group by treating the compound of Formula XXIX with a reducing agent, e.g., $LiAlH_4$, in an inert solvent (e.g., tetrahydrofuran) at an appropriate temperature (e.g. from about −78° C. to about 0° C.). The resulting alcohol can then be oxidized (e.g., under Swern conditions) to produce the compound of Formula XXXII where Y' is an aldehyde group. The aldehyde can then be converted to the corresponding alkene (i.e., a compound of Formula XXXII where Y' is a vinyl group), for example, by treatment with $Ph_3P=CH_2$. The alkene can then be hydrogenated (e.g., using $Rh/Al_2O_3$) to produce a compound of Formula XXXII where Y' is an ethyl group. For example, using this sequence of reactions in conjunction with a compounds of Formula XXIX in which $R^1$ and $R^3$, taken together with the atoms to which they are bonded, represent a phenyl ring; in which $R^{133}$ is a phenyl group; and in which $R^{134}$ is a 4-(2-chloroethoxy)phenyl group, and further treatment of the resulting compound of Formula XXXII where Y' is an ethyl group with dimethylamine in the presence of sodium iodide in $DMF-H_2O$ at appropriate temperature (e.g., about 55° C.), a cyclopropyl analog of tamoxifen can be produced. Using this method in conjunction with enantiomerically pure compounds of Formula XXIX (formed, for example, by using a dirhodium catalyst composition of the present invention containing a diastereomerically pure dirhodium catalyst), the stereochemistry of the chiral centers in this tamoxifen analog can be controlled. Further details regarding the conversion of Compounds of Formula XXIX to compounds of Formula XXXII can be found, for example, in Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters*, 2(6):823–826 (2000), which is hereby incorporated by reference.

Compounds of Formula XXXI can also be used to synthesize compounds having the formula ("Formula XXXIII"):

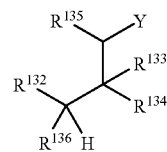

where each $R^{132}$, $R^{133}$, $R^{134}$, and Y are defined as they were with regard to Formula XXXI; where $R^{135}$ is a carboxylic acid group or a carboxylic acid derivative; and where $R^{136}$ represents an aryl group or an alkyl group. The synthesis includes providing a compound having Formula XXXI in which $R^{135}$ is a carboxylic acid group or a carboxylic acid derivative and converting this compound of Formula XXXI to the compound of Formula XXXIII using, for example, an aryl or alkyl cuprate (e.g., having the formula $[R^{136}]_2$CuLi$_2$CN).

Compounds of Formula XXXIII in which $R^{135}$ is a carboxylic acid group or a carboxylic acid derivative and in which $R^{132}$ has the formula:

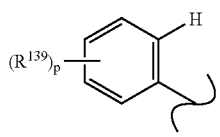

where each $R^{139}$ independently represents an alkyl group, an aryl group, a halogen, a hydroxy group, an amino group, a thiol group, an alkyl thiol group, an aryl thiol group or two or more of $R^{139}$, together with that atoms to which they are bonded, form a 5–12 membered ring; and where p represents an integer from 0 to 4 can be converted to compounds having the formula ("Formula XXXI V"):

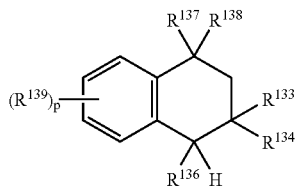

where each of $R^{133}$, $R^{134}$, and $R^{136}$ is defined as it was with regard to Formula XXXIII; where $R^{137}$ is H and $R^{138}$ represents an amino group or $R^{137}$ and $R^{138}$, together with the carbon atom to which they are bonded, represent a carbonyl moiety; and where $R^{139}$ is defined as above. For example, compounds of Formula XXXIII can be decarboxylated and then acylated (e.g., using a Friedel Crafts acylation method) to produce compounds of Formula XXXIV where $R^{137}$ and $R^{138}$, together with the carbon atom to which they are bonded, represent a carbonyl moiety. Reductive amination can be used to convert $R^{137}$ and $R^{138}$ from a=O group to an amine group.

Further details with regard to the aforementioned cyclopropanation reactions and the reactions which use the products of these cyclopropanation reactions can be found, for example, in Davies et al., "Asymmetric Cyclopropanations by Rhodium (II) N-(Arylsulfonyl)prolinate Catalyzed Decomposition of Vinyldiazomethanes in the Presence of Alkenes. Enantioselective Synthesis of the Four Stereoisomers of 2-Phenylcyclopropan-1-amino Acid," *J. Am. Chem. Soc.*, 118(29):6897–6907 (1996); Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters*, 2(6):823–826 (2000); Davies et al., "Effect of Diazoalkane Structure on the Stereoselectivity of Rhodium(II) (S)-N-(Arylsulfonyl)prolinate Catalyzed Cyclopropanations," *Tetrahedron Letters*, 37(24):4133–4136 (1996); Davies et al., "Effect of Catalyst on the Diastereoselectivity of Methyl Phenyldiazoacetate Cyclopropanations," *Tetrahedron Letters*, 39:8811–8812 (1998); Davies et al., "Enantioselective Synthesis of Fused Cycloheptadienes by a Tandem Intramolecular Cyclopropanation/Cope Rearrangement Sequence," *J. Org. Chem.*, 64(23):8501–8508 (1999); Davies, "Rhodium-Stabilized Vinylcarbenoid Intermediates in Organic Synthesis," *Current Organic Chemistry*, 2:463–488 (1998); Davies et al., "Effect of Rhodium Carbenoid Structure on Cyclopropanation Chemoselectivity," *Tetrahedron*, 56:4871–4880 (2000); Davies, "Dirhodium Tetra(N-arylsulfonylprolinates) as Chiral Catalysts For Asymmetric Transformations of Vinyl- and Aryldiazoacetates," *Eur. J. Org. Chem.*, pages 2459–2469 (1999); Nagashima et al., "Catalytic Asymmetric Solid-Phase Cyclopropanation," *J. Am. Chem. Soc.*, 123(11):2695–2696 (2001); and Davies, "Asymmetric Synthesis Using Rhodium-Stabilized Vinylcarbenoid Intermediates," *Aldrichimica Acta*, 30(4):107–114 (1997), each of which is hereby incorporated by reference. All of the cyclopropanation reactions set forth in the above-identified references can be modified by using the method and dirhodium catalyst compositions of the present invention. Illustratively, the dirhodium catalyst composition of the present invention can contain between one-half and 1/1000th of the amount of dirhodium catalyst called for in these references.

The above-described reactions exemplify the present invention's usefulness in catalyzing aryldiazomethane or vinyldiazomethane cyclopropanation reactions in which aryldiazomethanes or vinyldiazomethanes are contacted with a dirhodium catalyst composition according to the present invention under conditions effective to catalyze the aryldiazomethane or vinyldiazomethane cyclopropanation reaction. These methods provide new and useful ways to make compounds (such as the compounds illustrated by Formulae XXVII (in cases where $R^{130}$, $R^{131}$, and the carbon to which they are bonded form a cyclopropane moiety), XXIX, and XXXI–XXXIV) and to produce C—C bonds.

The method and composition of the present invention can also be used to produce optionally substituted cycloheptadienes or optionally substituted bicyclooctadienes. In this method, a diazo compound having the formula ("Formula XXXV"):

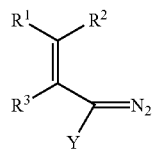

is provided. In Formula XXXV, Y is an electron withdrawing group; and $R^1$, $R^2$, and $R^3$ are independently selected from H, alkyl, aryl, silyloxy, or vinyl, or $R^1$ and $R^3$, together with the atoms to which they are bonded, form a 5–12 membered ring. The diazo compound having the Formula XXXV is then converted with a optionally substituted homocyclic, heterocyclic, or non-cyclic diene. Suitable optionally substituted homocyclic, heterocyclic, or non-cyclic diene include those having the formula ("Formula XXXVI"):

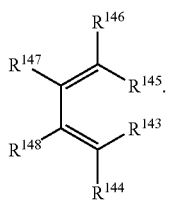

In Formula XXXVI, each of $R^{144}$, $R^{146}$, $R^{147}$, and $R^{148}$ independently represent an alkyl group, an aryl group, an alkoxy group, a halogen, hydrogen, an acyl group, a hydroxy group, a thiol group, an alkyl thiol or aryl thiol group, a carboxylic acid group, a carboxylic acid derivative, or a silyloxy group, or two or more of $R^{144}$, $R^{146}$, $R^{147}$, and $R^{148}$, together with the atom or atoms to which they are bonded, form a 5–12 membered ring. Each of $R^{143}$ and $R^{145}$ independently represents an alkyl group, an aryl group, an alkoxy group, a halogen, hydrogen, an acyl group, a hydroxy group, a thiol group, an alkyl thiol or aryl thiol group, a carboxylic acid group, a carboxylic acid derivative, or a silyloxy group, or $R^{143}$ and $R^{145}$ together represent a —O— moiety, a —S— moiety, a substituted or unsubstituted bivalent amino moiety (e.g., a substituted or unsubstituted bivalent amino moiety having the formula —N($R^{150}$)— in which $R^{150}$ is H, an aryl group, or alkyl group), or a substituted or unsubstituted methylene or ethylene moiety. Examples of optionally substituted cycloheptadienes or optionally substituted bicyclooctadienes that can be produced using this method include optionally substituted cyclohepta-1,5 dienes and optionally substituted 8-aza-bicyclo[3.2.1]octa-2,6 dienes, such as those having the formula ("Formula XXXVII"):

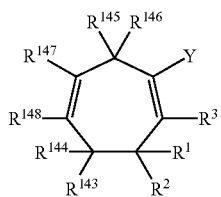

in which $R^{143}$, $R^{144}$, $R^{145}$, $R^{146}$, $R^{147}$, and $R^{148}$ have the same meanings as set forth above with regard to Formula XXXVI and in which $R^1$, $R^2$, $R^3$, and Y have the same meanings as set forth above with regard to Formula XXXV. The reaction is carried out using a dirhodium catalyst composition of the present invention. Other reaction conditions suitable for carrying out the conversion of compounds having Formula XXXV with optionally substituted homocyclic, heterocyclic, or non-cyclic diene are the same as those discussed above with regard to insertion reactions. The amount of catalyst used in this reaction can be between one-half and 1/1000th that which would be employed in the absence of the organic ester. For example, suitable mole ratios of the catalyst to the diazo compound of Formula XXXV are: from about $1:10^8$ to about 1:50, such as from about $1:10^7$ to about 1:100, from about $1:10^6$ to about 1:10,000, from about $1:10^8$ to about $1:10^7$, from about $1:10^8$ to about $1:10^6$, from about $1:10^8$ to about $1:10^5$, and/or from about $1:10^8$ to about $1:10^4$. Illustratively, the dirhodium catalyst and the diazo compound can be present in a mole ratio of greater than 2000:1, such as greater than about 5000:1, greater than about $10^4:1$, and/or greater than about $10^4:1$. Suitable organic ester: dirhodium catalyst mole ratios include mole ratios of from about 0.01:1 to about $10^8:1$, such as from about 0.1:1 to about $10^7:1$, from about 1:1 to about $10^6:1$, from about 10:1 to about $10^5:1$, from about 100:1 to about $10^4:1$, from about 100:1 to about $10^6:1$, and/or from about 1000:1 to about $10^6:1$. These reactions can be carried out stereospecifically, for example with enantiomerically pure dirhodium catalysts (such as enantiomerically pure dirhodium catalysts having $D_2$ symmetry), such as those depicted in Formulae IV and VII–XII. Alternatively, the reaction can be carried out racemically, in which case any dirhodium tetracarboxylate catalyst can be employed.

Compounds of Formula XXXVII in which $R^{143}$ and $R^{145}$ together represent a substituted or unsubstituted bivalent amino moiety having the formula —N($R^{150}$)— (in which $R^{150}$ is H, an aryl group, or alkyl group) can be readily converted to 3-aryltropanes, for example by reaction the compound of Formula XXXVII with a Grignard reagent (e.g., having the formula $R^{151}$—Mg—X, where $R^{151}$ is an aryl group and X is a halogen). Illustratively, the 3-aryltropane can have the formula ("Formula XXXVIII"):

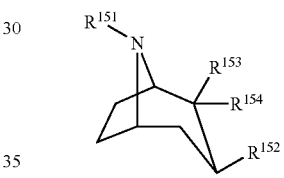

where $R^{151}$ is H, an aryl group, or an alkyl group; $R^{152}$ is an aryl group; $R^{153}$ represents H or a C1–C12 ketone; and $R^{154}$ represents H or a C1–C12 ketone. Further details regarding the dirhodium catalyzed preparation of cycloheptadienes and bicyclooctadienes, as well as the production of tropanes and other useful materials from these cycloheptadienes and bicyclooctadienes are available in U.S. Pat. No. 5,760,055 to Davies; U.S. Pat. No. 5,591,854 to Davies; Davies, "[3+4] Annulations Between Rhodium-Stabilized Vinylcarbenoids and Dienes," *Advances in Cycloaddition*, 5:119–164 (1999); Davies et al., "Tandem Asymmetric Cyclopropanation/Cope Rearrangement. A Highly Diastereoselective and Enantioselective Method for the Construction of 1,4-Cycloheptadienes," *J. Am. Chem. Soc.*, 120(4):3326–3331 (1998); Davies et al., "Enantioselective Synthesis of Functionalized Tropanes by Rhodium(II) Carboxylate-Catalyzed Decomposition of Vinyldiazomethanes in the Presence of Pyrroles," *J. Org. Chem.*, 62(4):1095–1105 (1997); Davies et al., "Effect of Rhodium Carbenoid Structure on Cyclopropanation Chemoselectivity," *Tetrahedron*, 56:4871–4880 (2000); Davies et al., "Enantioselective Synthesis of Fused Cycloheptadienes by a Tandem Intramolecular Cyclopropanation/Cope Rearrangement Sequence," *J. Org. Chem.*, 64(23):8501–8508 (1999); Davies, "Rhodium-Stabilized Vinylcarbenoid Intermediates in Organic Synthesis," *Current Organic Chemistry*, 2:463–488 (1998); and Davies, "Asymmetric Synthesis Using Rhodium-Stabilized Vinylcarbenoid Intermediates," *Aldrichimica Acta*, 30(4):107–114 (1997), each of which is hereby incorporated by reference.

The above-described reactions exemplify the present invention's usefulness in catalyzing [3+4] annulation reactions in which vinyldiazomethanes are reacted, for example, intermolecularly with a diene by contacting the vinyldiazomethane with a dirhodium catalyst composition of the present invention under conditions effective to produce a seven or eight membered ring or ring system. It should be noted that these reactions can also be carried out intramolecularly with a diene moiety contained in the vinyldiazomethane. These methods provide new and useful ways to make compounds (such as the compounds illustrated by Formulae XXXVII and XXXVIII) and to produce seven or eight membered rings and/or seven or eight membered ring systems (e.g., bicyclooctadiene ring systems).

The method and composition of the present invention can also be used to produce a compound having the formula ("Formula XXXIX"):

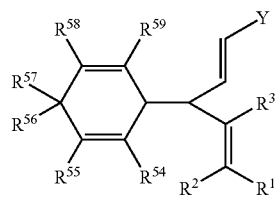

In Formula XXXIX, $R^1$, $R^2$, and $R^3$ are independently selected from H, alkyl, aryl, or vinyl, or $R^1$ and $R^3$, together with the atoms to which they are bonded, form a 5–12 membered ring, such as a cyclohexene ring, or a cyclohexa-1,3-diene ring. Illustratively, the method can be used to prepare compounds in which $R^1$ and $R^3$, together with the atoms to which they are bonded, form an aromatic ring, such as a 3,4-dichlorophenyl ring, in which case the compound produced can have the formula ("Formula XL"):

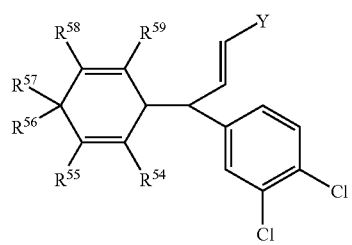

inn which Y is an electron withdrawing group, examples of which include moieties having the formulae: $-C(O)R^{77}$, $-SO_2R^{77}$, and $-P(O)R^{77}R^{77'}$. In these formulae, each of $R^{77}$ and $R^{77'}$ is independently selected from an alkyl group, an aryl group, and an alkoxy group. For example, Y can have the formula $CO_2R^{12}$ where $R^{12}$ is an alkyl group or an aryl group.

Each of $R^{54}$, $R^{55}$, $R^{56}$, $R^{57}$, $R^{58}$, and $R^{59}$ is independently selected from the group consisting of H, alkyl, aryl, halogen, and alkoxy.

The method includes providing a 1,3-cyclohexadiene having the formula ("Formula XLI"):

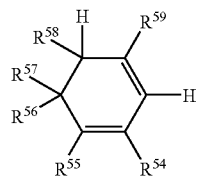

where $R^{54}$, $R^{55}$, $R^{56}$, $R^{57}$, $R^{58}$, and $R^{59}$ are defined as above with regard to Formula XL. The method further includes converting the 1,3-cyclohexadiene with a diazo compound having the formula ("Formula XLII"):

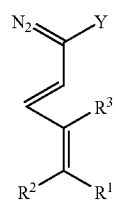

in which Y, $R^1$, $R^2$, and $R^3$ are as defined above.

Illustratively, the reaction can be carried out by combining the catalyst with the organic ester and then mixing this combination with the 1,3-cyclohexadiene of Formula XLI. Alternatively, the catalyst can be combined with the 1,3-cyclohexadiene of Formula XLI and the organic ester can be combined with the compound of Formula XLII, or vice versa. Still alternatively, the catalyst can be combined with the 1,3-cyclohexadiene of Formula XLI first, and then the organic ester can be added to this combination. In the case where the 1,3-cyclohexadiene of Formula XLI is a liquid (e.g., in the case where the compound of Formula XLI is 1,3-cyclohexadiene), this can be effected without the use of additional solvent. Alternatively, the mixture can be formed using an inert solvent or a solvent which is significantly less reactive towards the diazo compound of Formula XLII than is the compound of Formula XLI. Suitable solvents include alkanes, such as hexanes. The solvent can be dried prior to use using conventional methods; and the reaction vessel can also be dried, such as by flaming or in an oven. The amount of catalyst used in this reaction can be, for example, between one-half and $1/1000$th that which would be employed in the absence of the organic ester. For example, suitable mole ratios of the catalyst to the diazo compound of Formula XLII are: from about $1:10^8$ to about 1:50, such as from about $1:10^7$ to about 1:100, from about $1:10^6$ to about 1:10,000, from about $1:10^8$ to about $1:10^7$, from about $1:10^8$ to about $1:10^6$, from about $1:10^8$ to about $1:10^5$, and/or from about $1:10^8$ to about $1:10^4$. Illustratively, the dirhodium catalyst and the diazo compound can be present in a mole ratio of greater than 2000:1, such as greater than about 5000:1, greater than about $10^4:1$, and/or greater than about $10^4:1$. Suitable organic ester:dirhodium catalyst mole ratios include mole ratios of from about 0.01:1 to about $10^8:1$, such as from about 0.1:1 to about $10^7:1$, from about 1:1 to about $10^6:1$, from about 10:1 to about $10^5:1$, from about 100:1 to about $10^4:1$, from about 100:1 to about $10^6:1$, and/or from about 1000:1 to about 10⁶:1. The reaction is carried out using a dirhodium catalyst composition of the present invention.

Once the catalyst and compound of Formula XLI are mixed, the compound of Formula XLII is added, for example, with stirring. Addition can be carried out in a single portion, continuously, or batchwise. Slow, dropwise can be effected, for example, by using a syringe pump. The amount of compound of Formula XLII added is generally dependent on the amount of compound of Formula XLI present in the reaction mixture. For example, the mole ratio of compound of Formula XLII to compound of Formula XLI can be from about 1:10 to about 10:1, such as from about 1:8 to about 1:1 and/or from about 1:6 to about 1:4. The addition can be carried out at any suitable temperature from the freezing point to the boiling point of the solvent and/or the compound of Formula XLI. Illustratively, the addition can be carried out from about −50° C. to about 60° C., for example, at about room temperature. In certain embodiments, higher temperatures may favor a reverse Cope rearrangement, in which case, compounds having Formula XXXIX rearrange to form compounds having the formula ("Formula XLIII"):

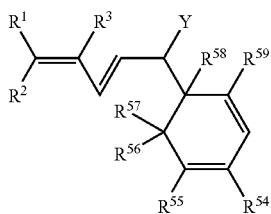

The method is suitable for making compounds having Formula XL which are substantially enantiomerically pure, such as, for example, compounds having the formula ("Formula XLIV"):

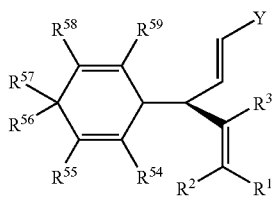

such as compounds having the formula ("Formula XLV"):

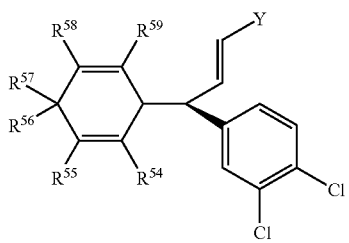

In one embodiment of the present invention, a substantially enantiomerically selective reaction is desired, and a chiral catalyst, such as one having $D_2$ symmetry, is employed. For example, by using one of the catalysts depicted in Formulae IV and VII–XII, compounds of Formulae XLIV and XLV which are substantially enantiomerically pure (e.g., >80% ee, >90% ee, >95% ee, >98% ee, and/or >99% ee) can be prepared.

The cyclohexadiene derivative of Formula XXXIX wherein $R^{57}$ is H can be converted into a compound having the formula ("Formula XLVI"):

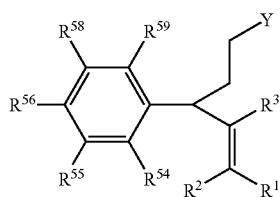

in which $R^1$, $R^2$, $R^3$, $R^{54}$, $R^{55}$, $R^{56}$, $R^{58}$, $R^{59}$, and Y are defined as they were above for the compounds having Formula XXXIX. The conversion can be carried out with hydrogenating and oxidizing agents under conditions effective to form the compound of Formula XLVI. The hydrogenation and oxidation reactions can be carried out simultaneously or sequentially, and, when carried out sequentially, hydrogenation can precede oxidation or oxidation can precede hydrogenation. Suitable hydrogenating agents for use in the present reaction include hydrogen gas in combination with a metal catalyst, such as palladium, (e.g., palladium on carbon). Suitable conditions for carrying out such reactions are described in House, *Modern Synthetic Reactions*, 2nd ed., Menlo Park, Calif.: The Benjamin/Cummings Publishing Company, pp. 1–34 (1972) ("House"), which is hereby incorporated by reference. Suitable oxidizing agents for use in the present reaction include those which are generally known to dehydrogenate 1,4-cyclohexadienyl moieties to phenyl moieties, such as 2,3-dichloro-5,6-dicyano-1,4-benzoquinone ("DDQ") and tetrachlorobenzoquinone (a.k.a., chloranil). Other suitable oxidizing agents and suitable conditions for carrying out such reactions are described, for example, at pages 33–44 of House, which is hereby incorporated by reference.

The above-described method is useful for making compounds having Formula XLVI in which Y is an alkoxycarbonyl group (e.g., in which Y has the formula —COOR¹² and R¹² is an alkyl group) and/or in which $R^1$ and $R^3$, together with the atoms to which they are bonded, form an aromatic ring, such as a 3,4-dichlorophenyl ring. In the latter case, the compound of Formula XLVI has the formula ("Formula XLVII"):

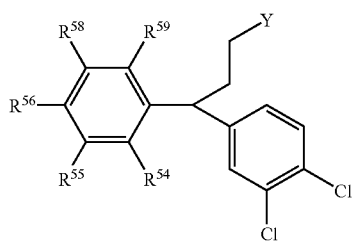

Furthermore, by using a cyclohexadiene having Formula XLIV (e.g., a cyclohexadiene having Formula XLV), substantially enantiomerically pure compounds of Formula XLVI, such as those having the formula ("Formula XLVIII"):

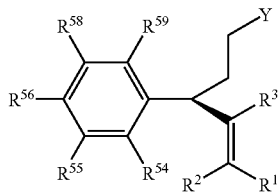

for example, those having the formula ("Formula XLIX"):

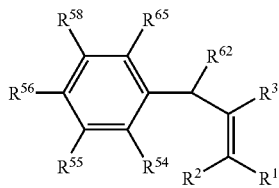

can be prepared.

The compound having Formula XLVI can be used to make a compound having the formula ("Formula L"):

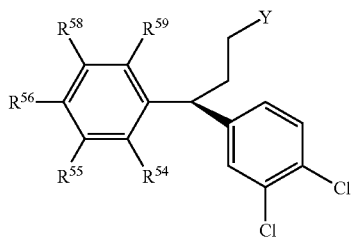

where $R^1$, $R^2$, $R^3$, $R^{54}$, $R^{56}$, and $R^{58}$ are defined as they were with regard to Formula XLVI. $R^{62}$ represents an alkyl moiety, examples of which include methyl, ethyl, or propyl groups, which can optionally be substituted with, for example, aryl groups (optionally containing a heteroatom) (e.g., pyrid-4-ylmethyl) or amino groups (which are meant to include amines that are unsubstituted or mono- or di-substituted with, for example, alkyl or aryl groups) (e.g., 2-(N,N-diisopropylamino)ethyl). Alternatively, $R^{65}$ and $R^{62}$ together represent the atoms necessary to complete a 5–12 membered ring, in which case the compound produced has the formula ("Formula LI"):

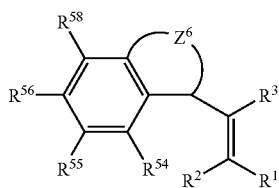

In this formula, $Z^6$ represents, for example, an alkylene group (e.g., a group having the formula —CH$_2$CH$_2$—, —CH$_2$CH$_2$CH$_2$—, —CH(NH$_2$)CH$_2$CH$_2$—, —CH$_2$CH$_2$CH (NH$_2$)—, —CH$_2$NRCH$_2$—, —CH$_2$CH(C$_6$H$_5$)CH$_2$—, etc.). Specific compounds of Formula L which can be made using this method include 1,1-diarylalkanes, such as the pharmaceuticals tolterodine and CDP-840, which respectively have the formulae:

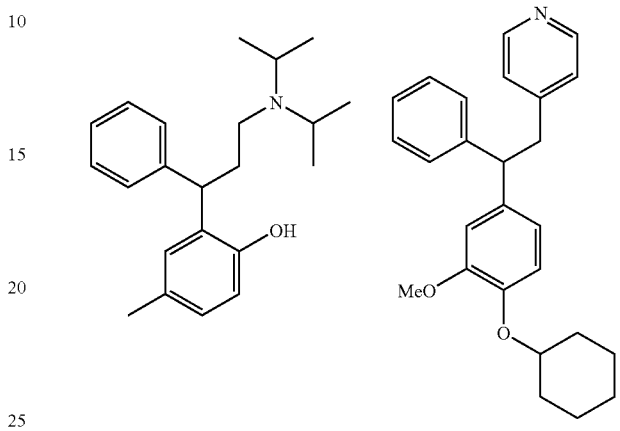

as well as nominfensine and sertraline, which respectively have the formulae:

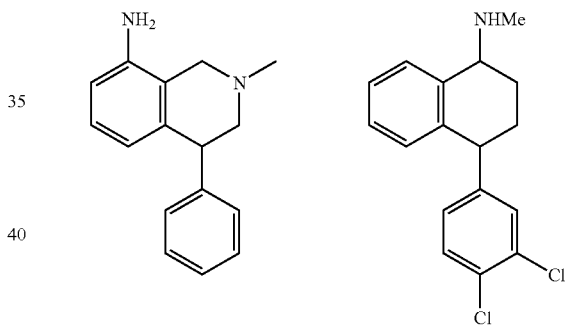

Conditions effective for achieving the conversion of compounds of Formula XLVI to compounds of Formula L depend on the nature of the desired substituents at $R^{62}$ and $R^{65}$. Illustratively, in the case where $R^{62}$ and $R^{65}$ are discreet moieties (i.e., in the case where $R^{62}$ and $R^{65}$ do not combine to form a ring structure), $R^{59}$ can be been chosen so that no further chemistry is required at that position to obtain the desired $R^{65}$ substituent, and the —CH$_2$CH$_2$Y moiety can be converted to the desired $R^{62}$ substituent using conventional methods. In the case where $R^{62}$ and $R^{65}$ combine to form a ring, conventional cyclization chemistry can be employed. For example, in the case where $R^{59}$ is H and $R^{62}$ and $R^{65}$ together represent a —CH$_2$CH$_2$CH$_2$— moiety, cyclization can be carried out using, for example, a Friedel-Crafts acylation catalyst.

The above method for making compounds having Formula LI is illustrated by the following procedure for making sertraline or sertraline congeners having the formula ("Formula LII"):

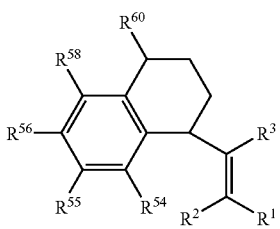

In Formula LII, $R^1$, $R_2$, $R^3$, $R^{54}$, $R^{55}$, $R^{56}$, and $R^{58}$ are defined as they were above with regard to compounds of Formula XLVI. $R^{60}$ is H. $R^{61}$ can represent a substituted or unsubstituted amine, such as an amine having the formula —$NR^{63}R^{64}$, where each of $R^{63}$ and $R^{64}$ is independently selected from hydrogen, an alkyl group, and an aryl group. Illustratively, $R^{61}$ can be a dialkyl amino group (e.g., $N(CH_3)_2$), a monoalkylamino group (e.g., —$NHCH_2CH_3$), or a monoarylamino group (e.g., —$NH(C_6H_5)$), or $R^{61}$ can represent a cyclic amine moiety, such as a piperidinyl group or a morpholino group. Alternately, $R^{60}$ and $R^{61}$, together with the carbon atom to which they are bonded, can represent a carbonyl (i.e., a C=O) moiety.

The method includes providing a cyclohexadiene derivative having Formula XXXIX in which Y is an electron withdrawing group, such as any one of the electron-withdrawing groups described above, and $R^{57}$ and $R^{59}$ are H. Cyclohexadiene derivatives which can be used in this reaction are those described above. Once the cyclohexadiene derivative is provided, it is converted with hydrogenating, oxidizing, and cyclizing agents under conditions effective to form the compound of Formula LII. The hydrogenation and oxidation reactions can be carried out simultaneously or sequentially, and, when carried out sequentially, hydrogenation can precede oxidation or oxidation can precede hydrogenation. Illustratively, both hydrogenation and oxidation can precede cyclization, as in the case where the cyclohexadiene derivative is converted with a hydrogenating agent and an oxidizing agent into a compound of Formula XLVI and where the phenyl derivative is then converted with a cyclizing agent under conditions effective to produce the compound.

Suitable hydrogenating and oxidizing agents and methods for their use are described above. Cyclizing agents suitable for use in the practice of the present invention include acylation catalysts, such as Friedel Crafts acylation catalysts, examples of which include $ClSO_3H$, $AlCl_3$, and other Lewis acids. In the case where Y is an alkoxycarbonyl group, the alkoxy group can be converted to a hydroxy group, prior to treatment with the Friedel Crafts acylation catalyst. This can be done using strong acid, e.g., 6 N HCl, or by any other suitable method. The immediate product of such a cyclization is a tetralone having the formula ("Formula LIII"):

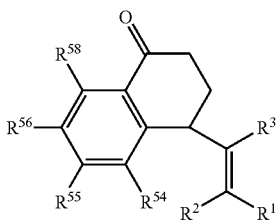

which can be readily converted to compounds having Formula LII by methods known to those skilled in the art, such as the reductive amination method set forth in Corey et al., *Tetrahedron Lett.*, 35:5373–5376 (1994), which is hereby incorporated by reference.

The above-described method is useful for making compounds having Formula LII in which Y is an alkoxycarbonyl group (e.g., in which Y has the formula —$COOR^{12}$ and $R^{12}$ is an alkyl group) and/or in which $R^1$ and $R^3$, together with the atoms to which they are bonded, form an aromatic ring, such as a 3,4-dichlorophenyl ring, in which case the compound of Formula LII can have the formula ("Formula LIV"):

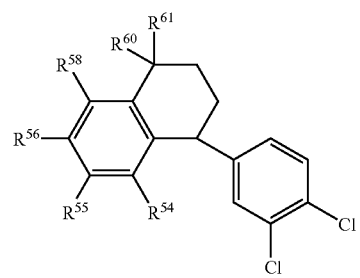

Furthermore, by using a cyclohexadiene having Formula XL (e.g., a cyclohexadiene having Formula XLV), substantially enantiomerically pure compounds of Formula LII, such as those having the formula ("Formula LV"):

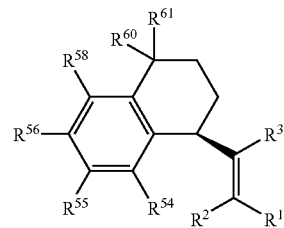

for example, those having the formula ("Formula LVI"):

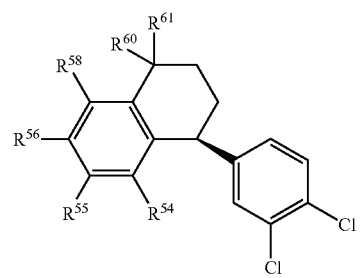

can be prepared.

Further details regarding these reactions as well as further discussion regarding the synthesis of diarylacetates, 4,4-diarylbutanoates, and other ω,ω-diarylalkanoates are set forth, for example, in Davies et al., "Catalytic Asymmetric Synthesis of Diarylacetates and 4,4-Diarylbutanoates. A Formal Asymmetric Synthesis of (+)-Sertraline," *Organic Letters*, 1(2):233–236 (1999), which is hereby incorporated by reference.

Other reactions that can benefit by the practice of the methods and use of the compositions of the present invention include those described in: Davies et al., "Effect of Carbenoid Structure on the Reactions of Rhodium-Stabilized Carbenoids with Cycloheptatriene," *Tetrahedron Letters*, 41:2035–2038 (2000), which is hereby incorporated by reference.

The present invention is further illustrated by the following non-limiting examples.

EXAMPLES

Example 1

Cyclopropanation Reactions with $Rh_2$(S-DOSP)$_4$ as Catalyst

In order to determine the minimum amount of catalyst that would be required to decompose diazo compounds, the reaction of styrene with phenyldiazoacetate using decreased amounts of $Rh_2$(S-DOSP)$_4$ along with and without methyl benzoate (1 equivalent based on the amount of phenyldiazoacetate) was examined. The results are presented in Table 1. All reactions were carried out at room temperature in hexanes. On using 0.1 mol % of $Rh_2$(S-DOSP)$_4$ (entries a and b in Table 1), the reaction proceeded with very good yield and ee but failed to reach completion with 0.01 moles of $Rh_2$(S-DOSP)$_4$ (entries c and d). Surprisingly with 1 equiv. of methyl benzoate and 0.01 mol % of $Rh_2$(S-DOSP)$_4$, (entries e and f in Table 1), decomposition of phenyl diazoacetate in presence of styrene resulted in high ee. The reaction did not reach completion when 0.001 mol % of $Rh_2$(S-DOSP)$_4$ was used. It was hypothesized that the drop in enantioselectivity could be due to the loss of the carboxylate ligands in $Rh_2$(S-DOSP)$_4$ (Davies et al., *J. Am. Chem. Soc.*, 118:6897 (1996), which is hereby incorporated by reference).

TABLE 1

| entry | amount of $Rh_2$ (S-DOSP)$_4$, mol % | additive, equiv. | isolated yield, % | ee, % | time |
|---|---|---|---|---|---|
| a | 0.1 | — | 98 | 90 | 1 h |
| b | 0.1 | 1 | 97 | 91 | 1 h |
| c | 0.01 | — | 62 | 25 | >60 h * |
| d | 0.01 | — | 57 | 28 | >60 h * |
| e | 0.01 | 1 | 96 | 85 | 16 h |
| f | 0.01 | 1 | 82 | 82 | 16 h |
| g | 0.001 | — | 15 | 11 | 8 d * |
| h | 0.001 | 1 | 14 | 10 | 8 d * |

* Reaction did not go to completion.

It has been observed that, for the bridged catalysts, when the arylsulfonyl group is a 2,4,6-triisopropylphenyl derivative of the compound of Formula XII, high asymmetric induction is achieved in the carbenoid reaction (Davies et al., *Tetrahedron Lett.*, 40:5287 (1999), which is hereby incorporated by reference). In order to confirm that the loss of the carboxylate ligands could be the reason for the drop in ee in low catalyst loading, cyclopropanation reactions were conducted using a bridged catalyst of Formula XII ($R^1=R^2$=2,4,6-triisopropyl-phenyl) and using methyl benzoate additive, as described in Example 2.

Example 2

Cyclopropanation Reactions with $Rh_2$(S-biTISP)$_2$ (Formula XII ($R^1=R^2$=2,4,6-triisopropyl-phenyl)) as Catalyst $Rh_2$(S-biTISP)$_2$ catalyzed decomposition of phenyldiazoacetate in the presence of styrene in $CH_2Cl_2$ at room temperature resulted in cyclopropanation product in 90% ee (Davies et al., *Tetrahedron Lett.*, 40:5287 (1999), which is hereby incorporated by reference). One of the most interesting and distinctive features of $Rh_2$(S-biTISP)$_2$ catalyzed reactions is that these reactions typically exhibit higher enantioselectivity in $CH_2Cl_2$ vis a vis hydrocarbon solvents (e.g., hexanes or pentanes). The reaction of styrene with phenyldiazoacetate using decreased amounts of $Rh_2$(S-biTISP)$_2$, with and without methyl benzoate as additive was carried out. The results are presented in Table 2.

TABLE 2

| entry | amount of $Rh_2$ (S-biTISP)$_2$, mol % | additive, equiv. | isolated yield, % | ee, % | time |
|---|---|---|---|---|---|
| a | 0.1 | — | 72 | 89 | 1 h |
| b | 0.1 | 1 | 82 | 89 | 1 h |
| c | 0.01 | — | X | X | X |
| d | 0.01 | 1 | 79 | 89 | 3 h |
| e | 0.001 | — | — | — | 6 d * |
| f | 0.001 | 1 | — | — | 6 d * |

* Reaction did not go to completion.

The cyclopropanation reaction took place smoothly at room temperature with 0.01% catalyst (ratio substrate/catalyst of 10,000) in the presence of methyl benzoate (entry d in Table 2). However cyclopropanation reaction with 0.001 mol % $Rh_2$(S-biTISP)$_2$ did not go to completion even after 6 d at room temperature. Encouraged by the marked activity of $Rh_2$(S-biTISP)$_2$ catalyst in cyclopropanation reactions, the reaction was carried out with 0.001% catalyst at higher temperature. Reaction of styrene with phenyldiazoacetate in the presence of 0.001% catalyst $Rh_2$(S-biTISP)$_2$ in refluxing dichloromethane (ca. 83° C.) resulted in high enantioselectivity as summarized in Table 3.

TABLE 3

| entry | amount of $Rh_2$ (S-biTISP)$_2$, mol % | additive, equiv. | isolated yield, % | ee, % | time |
|---|---|---|---|---|---|
| a | 0.01 | — | 60 | 86 | 1 h |
| b | 0.01 | 1 | 62 | 84 | 1 h |
| c | 0.001 | — | 64 | 83 | 16 h |
| d | 0.001 | 1 | 66 | 81 | 6 h |
| e | 0.0001 | — | 61 | 9 | 4 d |
| f | 0.0001 | 1 | 63 | 46 | — |

* Reaction did not go to completion.

However reaction with 0.0001% catalyst did not proceed to completion even after 4 days.

In order to achieve the goal of 1,000,000 turnover, reaction of phenyldiazoacetate with styrene in presence of 0.0001% catalyst in refluxing toluene (ca. 110° C.) was carried out. However it resulted in low enantioselectivity as shown in Table 4.

TABLE 4

| entry | amount of $Rh_2$ (S-biTISP)$_2$, mol % | additive, equiv. | isolated yield, % | ee, % | time |
|---|---|---|---|---|---|
| a | 0.01 | — | 79 | 63 | 1 h |
| b | 0.01 | 1 | 82 | 78 | 1 h |
| c | 0.001 | — | 75 | 29 | 4 h |
| d | 0.001 | 1 | 82 | 53 | 4 h |
| e | 0.0001 | — | 68 | 6 | 15 h |
| f | 0.0001 | 1 | 70 | 5 | 15 h |

The reaction of styrene with phenyldiazoacetate with 0.001 mol % catalyst in dichloromethane at room temperature did not go to completion even after 6 d (Table 2).

Since moisture could slow down the rate of formation of product, for example, by coordinating with catalyst or by reacting with the active carbenoid, the effect of molecular sieves was investigated. The cyclopropanation reaction of styrene with phenyldiazoace-tate using decreased amount of catalyst in $CH_2Cl_2$ in presence of molecular sieves (4 Å powder) with and without methyl benzoate additive was carried out at room temperature. The results are summarized in Table 5.

TABLE 5

| entry | amount of $Rh_2(S-biTISP)_2$, mol % | additive, equiv. | isolated yield, % | ee, % | time |
|---|---|---|---|---|---|
| a | 0.001 | — | 82 | 65 | 42 h |
| b | 0.001 | 1 | 85 | 83 | 28 h |
| c | 0.001 | 1 | X | X | 26 h |
| d | 0.0001 | — | 63 | 62 | 10 d * |
| e | 0.0001 | 1 | 75 | 74 | 10 d * |
| f | 1 | 1 | 87 | 85 | 1 h |

* Reaction did not go to completion.

Encouraged by the remarkable activity of the catalyst $Rh_2(S-biTISP)_2$ in cyclopropanation reaction of styrene, we then examined diphenylethylene as substrate. More particularly, the cyclopropanation reaction of diphenylethylene with phenyldiazoacetate using decreased amount of catalyst in dichloromethane in presence of molecular sieves (4 Å powder) with and without methyl benzoate additive was carried out at room temperature, and the results are summarized in Table 6.

TABLE 6

| entry | amount of $Rh_2(S-biTISP)_2$, mol % | additive, equiv. | isolated yield, % | ee, % | time |
|---|---|---|---|---|---|
| a | 0.001 | — | 85 | 76 | 36 h |
| b | 0.001 | 1 | 89 | 76 | 24 h |
| c | 0.0001 | — | — | 79 | 6 d * |
| d | 0.0001 | 1 | — | — | 6 d * |
| e | 1 | — | 88 | 78 | 1 h |

* Reaction did not go to completion.

In order to expand the scope of the reaction further, phenylbutadiene was also examined for cyclopropanation reaction with low amounts of catalyst. Phenylbutadiene was prepared in 75% yield in one step from trans-cinnamaldehyde by Wittig reaction with methyltri-phenylphosphonium-bromide $(Me(PPh_3)_3Br)$ in the presence of 1.6 M n-BuLi in tetrahydrofuran. Phenylbuta-diene was then reacted in a cyclopropanation reaction with phenyldiazoacetate using decreased amounts of catalyst in dichloromethane in presence of molecular sieves (4 Å powder) with and without methyl benzoate additive at room temperature. The results are summarized in Table 7.

TABLE 7

| entry | amount of $Rh_2(S-biTISP)_2$, mol % | additive, equiv. | isolated yield, % | ee, % | time |
|---|---|---|---|---|---|
| a | 1 | — | 90 | 79 | 1 h |
| b | 0.001 | 1 | 86 | 76 | 36 h |
| c | 0.001 | 1 | 92 | 78 | 28 h |

The cyclopropanation into styrene was extended to a range of aryldiazoacetates having the following formula:

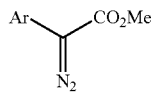

More particularly, the cyclopropanation reaction of aryldiazoacetates with phenyldiazoacetate was carried out using 0.001 mol % of $Rh_2(S-biTISP)_2$ in dichloromethane in presence of molecular sieves (4 Å powder) and in the presence of 1 equiv. of methyl benzoate additive at room temperature. The results are presented in Table 8. In all cases, the enantioselectivity and diastereoselectivity in these reactions were high.

TABLE 8

| entry | Ar | isolated yield, % | ee, % | time |
|---|---|---|---|---|
| a | 4-Br—$C_6H_4$ | 87 | 86 | 26 h |
|   | 4-Br—$C_6H_4$ | 86 | 87 | 30 h |
| b | 4-$CF_3$—$C_6H_4$ | 77 | 88 | 36 h |
|   | 4-$CF_3$—$C_6H_4$ | 76 | 87 | 36 h |
| c | 4-OMe—$C_6H_4$ | 94 | 68 | 24 h |
|   | 4-OMe—$C_6H_4$ | 91 | 80 | 26 h |
| d | 4-Me—$C_6H_4$ | 91 | 82 | 30 h |
| e | 1-naphthyl | 86 | 94 | 30 h |

To further illustrate the present invention, styrene was reacted with methylstyryldiazoacetate in presence of 0.01% $Rh_2(S-biTISP)_2$ catalyst in dichloromethane at room temperature in molecular sieves. The results are set forth in Table 9.

TABLE 9

| entry | amount of $Rh_2(S-biTISP)_2$, mol % | additive, equiv. | isolated yield, % | ee, % | time |
|---|---|---|---|---|---|
| a | 0.01 | — | 70 | 77 | 48 h |
| b | 0.01 | 1 | 77 | 85 | 48 h |
| c | 0.001 | — | NR | — | — |
| d | 0.001 | 1 | NR | — | — |

NR = no reaction;
* Reaction did not go to completion.

However reaction with 0.001% catalyst with and without methyl benzoate as additive gave no cyclopropanation product (entry c and d). Although the reason for this phenomenon has not been fully explored, applicant believes that the observed result may be due to the formation of the following pyrrazole which might poison the catalyst:

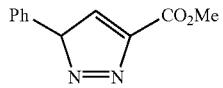

In any event, whether such a pyrrazole forms and whether it is responsible for poisoning the catalyst does not limit and is not be construed as limiting the scope of the present invention.

Finally as a control reaction, phenyldiazoacetate was reacted at room temperature with styrene in dichloromethane, in the presence of molecular sieves, but in the absence of catalyst. Less than 5% of the cyclopropantion product was observed by $^1$H NMR.

Example 3

Intermolecular C—H Insertion Reactions with Rh$_2$(S-biTISP)$_2$ (Formula XII (R$^1$=R$^2$=2,4,6-triisopropyl-phenyl)) as Catalyst Intermolecular C—H insertion reactions with low catalyst loading were then attempted, as shown in the following reaction scheme:

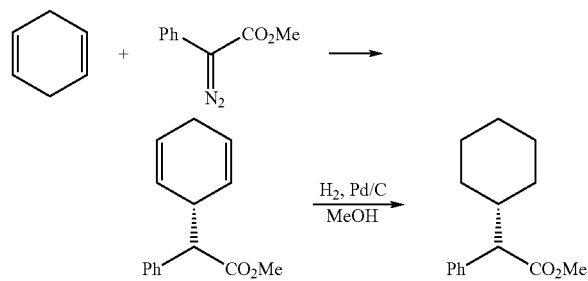

More particularly, Rh$_2$(S-biTISP)$_2$ (0.1 mol %) catalyzed the decomposition of phenyldiazoacetate in the presence of 1,4-cyclohexadiene in dichloromethane at room temperature in the presence of molecular sieves with methyl benzoate resulted in C—H insertion product. No trace of cyclopropanation product was observed. The diene was hydrogenated with H$_2$/Pd—C in methanol to give the cyclohexane derivative in 77% yield (two steps) and 15% ee.

Example 4

General Procedure for Cyclopropanation Reactions

Molecular Sieves (4 Å powder) were dried over 16 h at 150° C. under vacuum. Column chromatography was carried out on silica gel 60 (230–400) mesh. Enantiomeric excess was determined by HPLC using chiral analytical columns. Reactions were carried out under an atmosphere of argon. Hexanes were dried over and distilled from sodium metal with benzophenone as indicator. Methylene Chloride was dried over and distilled from calcium hydride. Degassing was carried out by bubbling Ar gas through the solution for 20 minutes.

Example 5

General Procedure for Rh(II)-Catalyzed Decomposition of Diazo Compounds in the Presence of Alkenes A solution of diazo compound (0.5 mmol, 1 equiv.) in dichloromethane (3 mL) was added over 1–2 h to a stirred solution of the alkene (2.5 mmol, 5 equiv.) and Rh(II) catalyst in dichloromethane (5 mL) at 23° C. under an argon atmosphere. The mixture was then stirred at 23° C. The mixture was then concentrated under reduced pressure, and the residue was purified on silica gel using pentane/ether (10:1) as the eluent.

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A dirhodium catalyst composition comprising:
   a dirhodium catalyst; and
   an organic ester, wherein said organic ester is not a substrate for catalysis by said dirhodium catalyst and wherein said organic ester is an ester of an aryl acid.

2. A composition according to claim 1, wherein said organic ester is an ester of a benzoic acid or an ester of a naphthoic acid.

3. A composition according to claim 1, wherein said organic ester is an ester of a benzoic acid.

4. A composition according to claim 1, wherein said organic ester is a C1–C12 alkyl ester of a benzoic acid.

5. A composition according to claim 1, wherein said organic ester has the formula C$_6$H$_5$COOW and wherein W is a C1–C12 alkyl group.

6. A composition according to claim 1, wherein said organic ester has the formula C$_6$H$_5$COOW and wherein W is a C1–C4 alkyl group.

7. A composition according to claim 1, wherein said organic ester has the formula C$_6$H$_5$COOW and wherein W is a methyl group.

8. A composition according to claim 1, wherein said dirhodium catalyst is a dirhodium tetracarboxylate catalyst.

9. A composition according to claim 8, wherein the dirhodium tetracarboxylate catalyst is selected from the group consisting of dirhodium acetate dimer, dirhodium propionate dimer, dirhodium butyrate dimer, dirhodium pentanoate dimer, dirhodium hexanoate dimer, dirhodium heptanoate dimer, dirhodium octanoate dimer, fluorinated analogs thereof, and combinations thereof.

10. A composition according to claim 8, wherein the dirhodium tetracarboxylate catalyst has the formula:

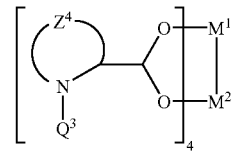

wherein each of M$^1$ and M$^2$ is Rh; Z$^4$ represents the atoms necessary to complete a 3–12 membered heterocyclic ring; and Q$^3$ is an electron withdrawing group.

11. A composition according to claim 10, wherein Z$^4$ has the formula —CH$^2$CH$^2$CH$^2$—.

12. A composition according to claim 11, wherein the dirhodium tetracarboxylate catalyst has one of the following formulae:

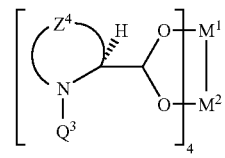

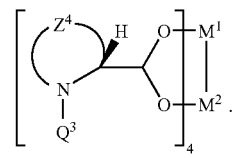

13. A composition according to claim 12, wherein the dirhodium catalyst has D$_2$ symmetry.

14. A composition according to claim 8, wherein the dirhodium tetracarboxylate catalyst has the formula:

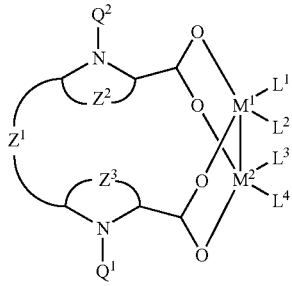

wherein each of $M^1$ and $M^2$ is Rh; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—$CR^{13}$—O—; $L^2$ and $L^4$, taken together, represent —O—$CR^{14}$—O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another.

15. A composition according to claim 14, wherein the dirhodium tetracarboxylate catalyst has the formula:

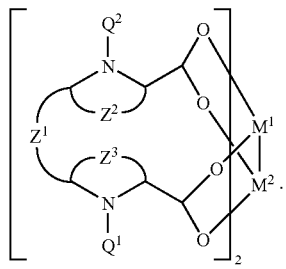

16. A composition according to claim 14, wherein $Z^2$ and $Z^3$ each have the formula —$CH_2CH_2$—.

17. A composition according to claim 14, wherein $Z^1$ is 1,3-phenylene.

18. A composition according to claim 14, wherein the dirhodium tetracarboxylate catalyst has one of the following formulae:

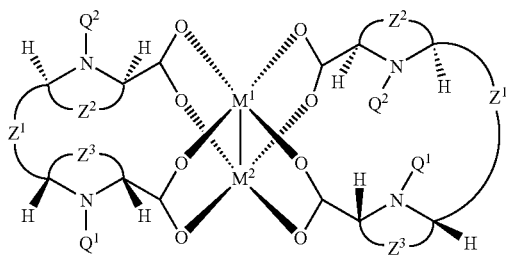

-continued

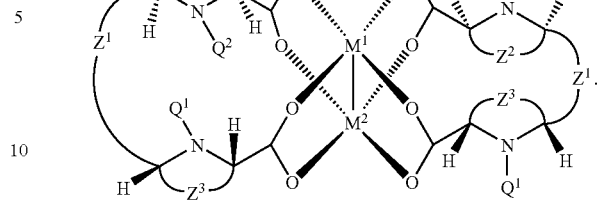

19. A composition according to claim 14, wherein the dirhodium tetracarboxylate catalyst has one of the following formulae:

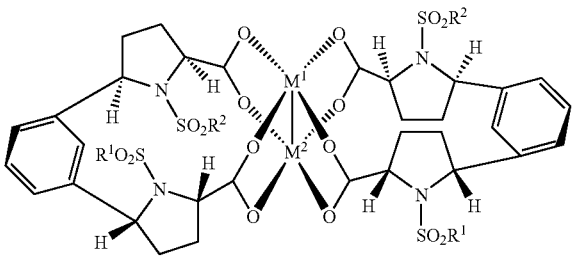

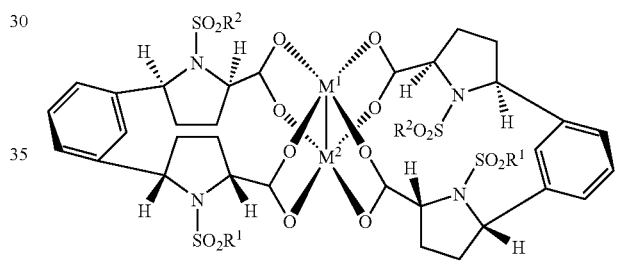

wherein $R^1$ and $R^2$ are the same or different and are alkyl or aryl groups.

20. A dirhodium catalyst composition a comprising:
a dirhodium catalyst; and
an organic ester, wherein said organic ester is not a substrate for catalysis by said dirhodium catalyst and wherein said organic ester and said dirhodium catalyst are present in a mole ratio of from 0.01:1 to $10^8$:1.

21. A composition according to claim 20, wherein said organic ester and said dirhodium catalyst are present in a mole ratio of from 0.1:1 to $10^7$:1.

22. A composition according to claim 20, wherein said organic ester and said dirhodium catalyst are present in a mole ratio of from 1000:1 to $10^6$:1.

23. A composition according to claim 20, wherein said organic ester and said dirhodium catalyst are present in a mole ratio of from 0.01:1 to $10^8$:1 and wherein said organic ester is an ester of a benzoic acid or an ester of a naphthoic acid.

24. A composition according to claim 1, wherein said organic ester and said dirhodium catalyst are present in a mole ratio of from 0.01:1 to $10^8$:1.

25. A composition according to claim 1, wherein said organic ester and said dirhodium catalyst are present in a mole ratio of from 0.1:1 to $10^7$:1.

26. A composition according to claim 1, wherein said organic ester and said dirhodium catalyst are present in a mole ratio of from 1000:1 to $10^6$:1.

27. A composition according to claim 1, wherein said organic ester and said dirhodium catalyst are present in a mole ratio of from 0.01:1 to $10^8$:1 and wherein said organic ester is an ester of a benzoic acid or an ester of a naphthoic acid.

* * * * *